(12) United States Patent
Herr

(10) Patent No.: US 8,551,184 B1
(45) Date of Patent: Oct. 8, 2013

(54) VARIABLE MECHANICAL-IMPEDANCE ARTIFICIAL LEGS

(75) Inventor: Hugh M. Herr, Somerville, MA (US)

(73) Assignee: iWalk, Inc., Bedford, MA (US)

( * ) Notice: Subject to any disclaimer, the term of this patent is extended or adjusted under 35 U.S.C. 154(b) by 0 days.

(21) Appl. No.: 13/363,820

(22) Filed: Feb. 1, 2012

Related U.S. Application Data

(63) Continuation of application No. 10/613,499, filed on Jul. 3, 2003.

(60) Provisional application No. 60/395,938, filed on Jul. 15, 2002.

(51) Int. Cl.
*A61F 2/70* (2006.01)
*A61F 2/66* (2006.01)

(52) U.S. Cl.
USPC .................. 623/24; 623/52; 623/47

(58) Field of Classification Search
None
See application file for complete search history.

(56) References Cited

U.S. PATENT DOCUMENTS

| | | | |
|---|---|---|---|
| 2,489,291 A | 11/1949 | Henschke et al. |
| 2,529,968 A | 11/1950 | Sartin |
| 3,098,645 A | 7/1963 | Owens |
| 3,207,497 A | 9/1965 | Schoonover |
| 3,844,279 A | 10/1974 | Konvalin |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |

(Continued)

FOREIGN PATENT DOCUMENTS

| | | |
|---|---|---|
| EP | 1393866 A1 | 3/2004 |
| EP | 1 408 892 | 4/2004 |

(Continued)

OTHER PUBLICATIONS

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003). 88 pages.

(Continued)

*Primary Examiner* — David H Willse
*Assistant Examiner* — Javier Blanco
(74) *Attorney, Agent, or Firm* — Wolf, Greenfield & Sacks, P.C.

(57) ABSTRACT

In one aspect, the invention provides methods and apparatus facilitating an adjustable-stiffness prosthesis or orthosis (including approximations to arbitrarily definable non-linear spring functions). Spring rates may be varied under no-load conditions during a walking gate cycle to minimize power consumption. In another aspect, the invention provides methods and apparatus for outputting positive power from a prosthesis or orthosis, facilitating high-performance artificial limbs. In one embodiment of the invention, the positive power is transferred from a functioning muscle to the prosthesis or orthosis, which mimics or assists a non-functioning or impaired muscle. In another embodiment of the invention, the positive power comes from an on-board power source in the prosthesis or orthosis.

25 Claims, 15 Drawing Sheets

Prosthetic Mechanisms Designed to Power Plantar-flex

(56) References Cited

U.S. PATENT DOCUMENTS

| | | |
|---|---|---|
| 4,697,808 A | 10/1987 | Larson et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,936,295 A | 6/1990 | Crane |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,282,460 A | 2/1994 | Boldt |
| 5,294,873 A | 3/1994 | Seraji |
| 5,311,109 A | 5/1994 | Ozawa |
| RE34,661 E | 7/1994 | Grim |
| 5,327,790 A | 7/1994 | Levin et al. |
| 5,330,417 A | 7/1994 | Petersen et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,888,213 A | 3/1999 | Sears et al. |
| 5,898,948 A | 5/1999 | Kelly et al. |
| 5,910,720 A | 6/1999 | Williamson et al. |
| 5,932,230 A | 8/1999 | DeGrate |
| 5,944,760 A | 8/1999 | Christensen |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,095,991 A | 8/2000 | Krausman et al. |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,500,138 B1 | 12/2002 | Irby et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,532,400 B1 | 3/2003 | Jacobs |
| 6,585,774 B2 | 7/2003 | Dean, Jr. et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,645,252 B2 | 11/2003 | Asai et al. |
| 6,660,042 B1 | 12/2003 | Curcie et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| 6,821,233 B1 | 11/2004 | Colombo et al. |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,942,629 B2 | 9/2005 | Hepburn et al. |
| 6,945,947 B2 | 9/2005 | Ingimundarson et al. |
| 6,966,882 B2 | 11/2005 | Horst |
| 6,969,408 B2 | 11/2005 | Lecomte et al. |
| 6,992,455 B2 | 1/2006 | Kato et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,190,141 B1 | 3/2007 | Ashrafiuon et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,278,954 B2 | 10/2007 | Kawai et al. |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |

| | | |
|---|---|---|
| 7,390,309 B2 | 6/2008 | Dariush |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,628,766 B1 | 12/2009 | Kazerooni et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,770,842 B2 | 8/2010 | Benson |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,874,223 B2 | 1/2011 | Sugar et al. |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| 7,985,265 B2 | 7/2011 | Moser et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,142,370 B2 | 3/2012 | Weinberg et al. |
| 8,181,520 B2 | 5/2012 | Kadota et al. |
| 8,202,325 B2 | 6/2012 | Albrecht-Laatsch et al. |
| 8,287,477 B1 | 10/2012 | Herr et al. |
| 8,419,804 B2 | 4/2013 | Herr et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0083528 A1 | 5/2004 | Stewart et al. |
| 2004/0088025 A1 | 5/2004 | Gesotti |
| 2004/0181118 A1 | 9/2004 | Kochamba |
| 2004/0181289 A1 | 9/2004 | Bedard et al. |
| 2004/0255711 A1 | 12/2004 | Takenaka et al. |

| | | |
|---|---|---|
| 2004/0261561 A1 | 12/2004 | Takenaka et al. |
| 2005/0007834 A1 | 1/2005 | Hidaka |
| 2005/0043614 A1 | 2/2005 | Huizenga et al. |
| 2005/0049652 A1 | 3/2005 | Tong |
| 2005/0059908 A1 | 3/2005 | Bogert |
| 2005/0070834 A1 | 3/2005 | Herr et al. |
| 2005/0085948 A1 | 4/2005 | Herr et al. |
| 2005/0155444 A1 | 7/2005 | Otaki et al. |
| 2005/0179417 A1 | 8/2005 | Takenaka et al. |
| 2005/0197717 A1 | 9/2005 | Ragnarsdottir et al. |
| 2005/0209707 A1 | 9/2005 | Phillips et al. |
| 2005/0228515 A1 | 10/2005 | Musallam et al. |
| 2006/0004299 A1 | 1/2006 | Endo et al. |
| 2006/0004307 A1 | 1/2006 | Horst |
| 2006/0055358 A1 | 3/2006 | Ogawa et al. |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0135883 A1 | 6/2006 | Jonsson |
| 2006/0173552 A1 | 8/2006 | Roy |
| 2006/0211956 A1 | 9/2006 | Sankai |
| 2006/0213305 A1 | 9/2006 | Sugar et al. |
| 2006/0214621 A1 | 9/2006 | Ogawa et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0156252 A1 | 7/2007 | Jonsson et al. |
| 2007/0162152 A1 | 7/2007 | Herr et al. |
| 2007/0233279 A1 | 10/2007 | Kazerooni et al. |
| 2007/0267791 A1 | 11/2007 | Hollander et al. |
| 2008/0039756 A1 | 2/2008 | Thorsteinsson et al. |
| 2008/0114272 A1 | 5/2008 | Herr et al. |
| 2008/0155444 A1 | 6/2008 | Pannese et al. |
| 2008/0161937 A1 | 7/2008 | Sankai |
| 2008/0234608 A1 | 9/2008 | Sankai |
| 2009/0030530 A1 | 1/2009 | Martin |
| 2009/0171469 A1 | 7/2009 | Thorsteinsson et al. |
| 2009/0192619 A1 | 7/2009 | Martin et al. |
| 2009/0222105 A1 | 9/2009 | Clausen |
| 2010/0004860 A1 | 1/2010 | Chernoguz et al. |
| 2010/0025409 A1 | 2/2010 | Hunter |
| 2010/0094188 A1 | 4/2010 | Goffer et al. |
| 2010/0113980 A1 | 5/2010 | Herr et al. |
| 2010/0114329 A1 | 5/2010 | Casler et al. |
| 2010/0174384 A1 | 7/2010 | Herr et al. |
| 2010/0174385 A1 | 7/2010 | Casler et al. |
| 2010/0179668 A1 | 7/2010 | Herr et al. |
| 2010/0312363 A1 | 12/2010 | Herr et al. |
| 2011/0082566 A1 | 4/2011 | Herr et al. |
| 2011/0105966 A1 | 5/2011 | Kazerooni et al. |
| 2011/0224804 A1 | 9/2011 | Clausen et al. |
| 2011/0245931 A1 | 10/2011 | Clausen et al. |
| 2011/0257764 A1 | 10/2011 | Herr et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2011/0295384 A1 | 12/2011 | Herr et al. |
| 2011/0295385 A1 | 12/2011 | Herr et al. |
| 2012/0209405 A1 | 8/2012 | Herr et al. |
| 2012/0259429 A1 | 10/2012 | Han et al. |
| 2012/0259430 A1 | 10/2012 | Han et al. |
| 2012/0259431 A1 | 10/2012 | Han et al. |
| 2012/0271433 A1 | 10/2012 | Galea et al. |
| 2012/0283845 A1 | 11/2012 | Herr et al. |

FOREIGN PATENT DOCUMENTS

| | | |
|---|---|---|
| EP | 1 534 117 | 6/2005 |
| JP | 2005-000500 | 1/2005 |
| WO | WO9409727 A2 * | 5/1994 |
| WO | WO-03068453 A1 | 8/2003 |
| WO | WO-2004017872 A1 | 3/2004 |
| WO | WO-2004019832 A1 | 3/2004 |
| WO | WO 2006/110895 | 10/2006 |
| WO | WO 2007/025116 A2 | 3/2007 |
| WO | WO 2009/082249 | 7/2009 |
| WO | WO 2010/025403 A1 | 3/2010 |
| WO | WO 2010/025409 | 3/2010 |
| WO | WO-2010027968 A2 | 3/2010 |
| WO | WO 2011/005482 A2 | 1/2011 |

OTHER PUBLICATIONS

Dollar, et al., "Lower Extremity Exoskeletions and Active Orthoses: Challenges and State-of-the-Art," IEEE Transcations on Robotics, vol. 24, No. 1, Feb. 2008, 15 pages.

Hogan, N., "Impedance Control: An Approach to Manipulation," Dept. of Mechanical Engineering and Labortory of Manufacturing and Productivity, Massachusetts Institute of Technology, Cambridge MA, pp. 304-313, (Jun. 1984).

Hogan, N., "Impedance Control: An Approach to Manipulation: Part II—Implementation," Journal of Dynamic Systems, Measurement, and Control, 107:8-16, (1985).

Hogan, N., Impedance Control: An Approach to Manipulation: Part III—Application, Journal of Dynamics Systems, Measurement, and Control, 107:17-24, (1985).

Kim, et al., "Realization of Dynamic Walking for the Humaniod Robot Platform KHR-1," Advanced Robotics, vol. 18, No. 7, pp. 749-768, (2004).

Klute et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., Oct. 1-3, 1998, p. 52.

Klute, et al., "Artificial Muscles: Actuators for Biorobotic Systems," The International Journal of Robotics Research, vol. 21, No. 4, Apr. 2002, pp. 295-309.

Klute, et al., Artificial Muscles: Actuators for Lower Limb Prostheses, Abstract in: Proceedings of the 2nd Annual Meeting of the VA rehabilitation Research and Development Service, Feb. 20-22, 2000, p. 107.

Klute, et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.

Klute, et al., Intelligent Transtibial Prostheses with Muscle-Like Actuators,: 2002 American Physiological Society Intersociety Meeting: The Power of Comparative Physiology: Evolution, Integration, and Applied, 1 page.

Klute, et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.

Klute, et al., "McKibben Artificial Muscles: Pneumatic Actuators with Biomechanical Intelligence," IEEE/ASME 1999 Inernational Conference on Advanced Intelligent Mechatronics, Atlanta, GA, Sep. 19-22, 1999, pp. 221-226.

Klute, et al., "Muscle-Like Pneumatic Actuators for Below-Knee Prostheses," Actuator2000:7th International Conference on New Actuators, Bremen, Germany on Jun. 9-21, 2000, pp. 289-292.

International Search Report and Written Opinion for PCT/US2009/055600 mailed Apr. 29, 2010 (23 pages).

International Search Report and Written Opinion for PCT/US2010/047279 mailed Jan. 19, 2011 (11 pages).

International Search Report and Written Opinion for PCT/US2011/031105 mailed Oct. 11, 2011 (16 pages).

Abbas J. and Chizeck H., "Neural Network Control of Functional Neuromuscular Stimulation Systems: Computer Simulation Studies," IEEE Transactions on Biomedical Engineering, vol. 42, No. 1, Nov. 1995, pp. 1117-1127.

Abul-haj, C. and Hogan, N., "Functional assessment of control systems for cybernetic elbow prostheses. Part I, Part II," IEEE Transactions on Biomedical Engineering, vol. 37, No. 11, Nov. 1990, Cambridge, MA, pp. 1025-1047.

Akazawa, K., et. al, "Biomimetic EMG prosthesis-hand," Proceedings of the 18th Annual International Conference of the IEEE Engineering in Medicine and Biology Society, vol. 2, Oct. 1996, Amsterdam, Netherlands, pp. 535-536.

Aminian, "Estimation of Speed and Incline of Walking Using Neural Network," IEEE Transactions on Biomedical Engineering, vol. 44, No. 3, Jun. 1995, pp. 743-746.

Anderson, F. and Pandy M., "Dynamic optimization of human walking," Journal of Biomechanical Engineering, vol. 123, Oct. 2001, pp. 381-390.

Andrews, et al., "Hybrid FES Orthosis incorporating closed loop control and sensory feedback," J. Biomed Eng., vol. 10, Apr. 1988, pp. 189-195.

Arakawa, T. and Fukuda, T., "Natural motion generation of biped locomotion robot using hierarchical trajectory generation method consisting of GA, EP layers," Proceedings of the 1997 IEEE International Conference on Robotics and Automation, Apr. 1997, Albuquerque, NM, pp. 211-216.

Au., et. al., "Powered Ankle-Foot Prosthesis for the Improvement of Amputee Ambulation," Proceedings of the 29th Annual International Conference of the IEEE, Aug. 2007, Lyon, France, pp. 3020-3026.

Au, S. and Herr H., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.

Au, S., et al. "An ankle-foot emulation system for the study of human walking biomechanics," Proc. of the 2006 IEEE Int. Conf. on Robotics and Automation, May 2006, Orlando, FL, pp. 2939-2945.

Au, S., et. al., "Biomechanical design of a powered ankle-foot prosthesis," Proc. of the 2007 IEEE Int. Conf. on Rehabilitation Robotics, Jun. 2007, Noordwijk, Netherlands, pp. 298-303.

Au, S., et. al., "Powered ankle-foot prosthesis to assist level-ground and stair-descent gaits," Neural Networks, vol. 21, No. 4, Mar. 2008, pp. 654-666.

Au, S., "An EMG-position controlled system for an active ankle-foot prosthesis: an initial experimental study," Proc. of the 2006 IEEE International Conference on Rehabilitation Robotics, Jul. 2005, Chicago, IL, pp. 375-379.

Au, S., et. al., "Powered Ankle-foot Prosthesis Improves Walking Metabolic Economy," IEEE Trans. on Robotics, vol. 25, No. 1, Feb. 2009, pp. 51-66.

Barth, D.., et. al., "Gait analysis and energy cost of below-knee amputees wearing six different prosthetic feet," Journal of Prosthetics & Orthotics, vol. 4, No. 2, Winter, 1992, pp. 63-75.

Baten, et al., "Inertial Sensing in Ambulatory back load Estimation," 18 Annual International Conferences of IEEE Engineering in Medicine and Biology Society, Amsterdam 1996, pp. 497-498.

Bateni, H. and Olney S., "Kinematic and kinetic variations of below-knee amputee gait," Journal of Prosthetics & Orthotics, vol. 14, No. 1, Mar. 2002, pp. 2-13.

Blaya, J. and Herr, H, "Adaptive control of a variable-impedance ankle-foot orthosis to assist drop-foot gait," IEEE Transactions on Neural Systems and Rehabilitation Engineering, vol. 12, No. 1, Mar. 2004, pp. 24-31.

Blickhan, R., "The spring-mass model for running and hopping," J of Biomech. 22, Feb. 1989, Great Britain, pp. 1217-1227.

Bortz, "A New Mathematical Formulation for Strapdown Inertial Navigation," IEEE Transactions of Aerospace and Electronic Systems, vol. AES-7, No. 1, Jan. 1971, p. 61-66.

Brockway, J., "Derivation of formulae used to calculate energy expenditure in man," Human Nutrition Clinical Nutrition, vol. 41, Nov. 1987, pp. 463-471.

Brown, R., "On the nature of the fundamental activity of the nervous centres: together with an analysis of the conditioning of rhythmic activity in progression, and a theory of the evolution of function in the nervous system," J Physiol, vol. 48, No. 1, Mar. 1914, pp. 18-46.

Chang, et al., Ischemic Colitis and Complications of Constipation Associated with the use of Alosetron Under a Risk Management Plan: Clinical Characteristics, Outcomes, and Incidences The Americal Journal of Gastroenterology, vol. 105, No. 4, Apr. 2010, pp. 866-875.

Chu, A., Kazerooni, H. And Zoss, A., "On the Biomimetic Design of the Berkeley Lower Extremity Exoskeleton (BLEEX)," Proceedings of the 2005 IEEE International Conference on Robotics and Automation, Apr. 2005, Barcelona, Spain, pp. 4356-4363.

Colborne, G. R., S. Naumann, P. E. Longmuir, and D. Berbrayer, "Analysis of mechanical and metabolic factors in the gait of congenital below knee amputees," Am. J. Phys. Med. Rehabil., vol. 92, pp. 272-278, Oct. 1992.

Collins, et al., "Supporting Online Material for Efficient bipedal robots based on passive-dynamic walkers," Mechanical Engineering, University of Michigan, Feb. 2005, Ann Arbor, MI, pp. 1-8.

Collins, et al., "Controlled Energy Storage and Return Prosthesis Reduces Metabolic cost of Walking," ASB 29$^{th}$ Annual Meeting, Cleveland, Ohio, Jul. 31-Aug. 5, 2005, 1 page.

Crago P., et. al., "New Control Strategies for neuroprosthetic systems," Journal of Rehabilitation Research and Development, vol. 33, No. 2, Apr. 1996, pp. 158-172.

Daley, M. A., Felix, G., Biewener, A. A., 2007. Running stability is enhanced by a proximo-distal gradient in joint neuromechanical control. J Exp Biol 210 (Pt 3), Nov. 2006, pp. 383-394.

Dapena, J. and McDonald, C., "Three-dimensional analysis of angular momentum in the hammer throw," Med. Sci. in Sports Exerc., vol. 21, No. 2, Apr. 1989, pp. 206-220.

Dietz, V., "Proprioception and locomotor disorders," Nat Rev Neurosci, vol. 3, Oct. 2002, pp. 781-790.

Dietz, V., "Spinal Cord Pattern Generators for Locomotion," download Feb. 6, 2012, http://www.Clinph-journal.com/article/PIIS1388245703001202/fulltext, 12 pages.

Doerschuk, et. al., "Upper extremity limb function discrimination using EMG signal analysis," IEEE Transactions on Biomedical Engineering. vol. 30., No. 1., Jan. 1983, pp. 18-28.

Doke, J., et. al., "Mechanics and energetics of swinging the human leg," The Journal of Experimental Biology, vol. 208, Feb. 2005, pp. 439-445.

Donelan, J., et. al., "Force regulation of ankle extensor muscle activity in freely walking cats," J Neurophysiol, vol. 101, No. 1, Nov. 2008, pp. 360-371.

Donelan, J., et. al., "Mechanical work for step-to-step transitions is a major determinant of the metabolic cost of human walking," J. Exp. Biol., vol. 205, Dec. 2002, pp. 3717-3727.

Donelan, J., et. al. "Simultaneous positive and negative external mechanical work in human walking," Journal of Biomechanics, vol. 35, Jan. 2002, pp. 117-124.

Drake, C., "Ankle & Foot Splints or Orthoses," HemiHelp, Information Sheet 13 Last updated Jun. 2009, 5 pages.

Drake, C., "Ankle & Foot Splints or Orthoses (AFOs)," HemiHelp, Last updated Jun. 2009, 8 pages.

Drake, C., "Foot & Ankle Splints or Orthoses," HemiHelp Information Sheet, London, United Kingdom, www.hemihelp.org.uk/leaflets/hbleaflets90.htm, pp. 1-3.

Eilenberg, M., "A Neuromuscular-Model Based Control Strategy for Powered Ankle-Foot Prostheses," Masters Thesis, Massachusetts Institute of Technology, Cambridge, Mass., 2009.

Ekeberg, O. and Grillner, S., "Simulations of neuromuscular control in lamprey swimming," Philos Trans R Soc Lond B Biol Sci, vol. 354, May 1999, pp. 895-902.

Ekeberg, O. and Pearson, K., "Computer simulation of stepping in the hind legs of the cat: an examination of mechanisms regulating the stance-to-swing transition," J Neurophysiol, vol. 94, No. 6, Jul. 2005, pp. 4256-4268.

Endo, K., et. al., "A quasi-passive model of human leg function in level-ground walking," Proc. of 2006 IEEE/RSJ International Conference on Intelligent Robots and Systems (IROS), Oct. 2006, Beijing, China, pp. 4935-4939.

Eppinger, S. Seering W., "Three dynamic problems in robot force control," IEEE Transactions on Robotics and Automation, vol. 8, No. 6, Dec. 1992, pp. 751-758.

Esquenazi, A. and DiGiacomo, R., "Rehabilitation After Amputation," Journ Am Podiatr Med Assoc, vol. 91, No. 1, Jan. 2001, pp. 13-22.

Farley, C. and McMahon, T., "Energetics of walking and running: insights from simulated reduced-gravity experiments," The American Physiological Society, Dec. 1992, pp. 2709-2712.

Farry, K. A., et al., "Myoelectric teleoperation of a complex robotic hand," IEEE Transactions on Robotics and Automation. vol. 12, No. 5, Oct. 1996, pp. 775-788.

Featherstone, R., 1987, "Robot Dynamic Algorithms", Boston, Mass., Kluwer Academic Publishers, pp. 155-172.

Fite, K., et. al., "Design and Control of an Electrically Powered Knee Prosthesis," Proc. of 2007 IEEE 10th International Conference on Rehabilitation Robotics (ICORR), Jun. 2007, pp. 902-905.

Flowers, W. "A Man-Interactive Simulator System for Above-Knee Prosthetic Studies," Ph.D. thesis, Massachusetts of Institute Technology, Department of Mechanical Engineering. Jul. 10, 1973.

Fod, A., et. al., "Automated Derivation of Primitives for Movements Classification," Autonomous Robots, vol. 12, No. 1, Jan. 2002, pp. 39-54.

Frigon, A. and Rossignol, S., "Experiments and models of sensorimotor interactions during locomotion," Biol Cybern, vol. 95, No. 6, Nov. 2006, pp. 607-627.

Fujita K, et. al., "Joint angle control with command filter for human ankle movement using functional electrical stimulation," Proc. of IEEE Ninth Annual Conference for the Engineering in Medicine and Biology Society, Nov. 1987, Boston, MA, pp. 1719-1720.

Fukuda, O. et al., "A human-assisting manipulator teleoperated by EMG signals and arm motions," IEEE Transactions on Robotics and Automation. vol. 19, No. 2, Apr. 2003, pp. 210-222.

Gates, D., "Characterizing ankle function during stair ascent, descent, and level walking for ankle prosthesis and orthosis design," Master's thesis, Boston University, 2004, pp. 1-82.

Geiritsen, K., et. al., "Direct dynamics simulation of the impact phase in heel-toe running," J. Biomech., vol. 28, No. 6, Jun. 1995, Great Britain, pp. 661-668.

Geyer, H., et. al., "Positive force feedback in bouncing gaits?," Proceedings of Royal Society B-Biological Sciences, vol. 270, No. 1529, Aug. 2003, pp. 2173-2183.

Geyer, H. and Herr H., "A muscle-reflex model that encodes principles of legged mechanics predicts human walking dynamics and muscle activities," IEEE Transactions on Neural Systems and Rehabilitations Engineering, vol. 18, No. 3, Jun. 2010, pp. 263-273.

Geyer, H., et. al., "Compliant leg behaviour explains the basic dynamics of walking and running," Proc. R. Soc. Cond. B 273, Aug. 2006, pp. 2861-2867.

Ghigliazza, R., et. al., "A simply stabilized running model," SIAM J. Applied. Dynamical Systems, vol. 2, No. 2, May 2004, pp. 187-218.

Godha, el al., "Integrated GPS/INS System for Pedestrian Navigation in a Signal Degraded Environment," ION GNSS, Sep. 2006, Fort Worth, TX, pp. 1-14.

Goswami, A., "Postural stability of biped robots and the foot-rotation indicator (FRI) point," International Journal of Robotics Research, vol. 18, No. 6, Jun. 1999, pp. 523-533.

Goswami, A. and Kallem, V., "Rate of change of angular momentum and balance maintenance of biped robots," Proceedings of the 2004 IEEE International Conference on Robotics and Automation, Apr. 2004, New Orleans, La., pp. 3785-3790.

Graupe, D., et al., "A microprocessor system for multifunctional control of upper-limb prostheses via myoelectric signal identification," IEEE Transaction on Automatic Control. vol. AC-23, vol. 4, Aug. 1978, pp. 538-544.

Gregoire, L., and et al, "Role of mono- and bi-articular muscles in explosive movements," International Journal of Sports Medicine 5, 614-630. Dec. 1984.

Grillner, S. and Zangger, P., "On the central generation of locomotion in the low spinal cat," Exp Brain Res, vol. 34, No. 2, Jan. 1979, pp. 241-261.

Grimes, D. L., "An active multi-mode above-knee prosthesis controller," Ph.D. Thesis, Massachusetts Institute of Technology, Jul. 20, 1979.

Gu, W., "The Regulation of Angular Momentum During Human Walking," Undergraduate Thesis, Massachusetts Institute of Technology, Physics Department, Jun. 2003, pp. 2-48.

Gunther, M., et. al., "Human leg design: optimal axial alignment under constraints," J. Math. Biol., vol. 48, Mar. 2004, pp. 623-646.

Gunther, M. and Ruder, H., "Synthesis of two-dimensional human walking: a test of the A-model," Biol. Cybern., vol. 89, May 2003, pp. 89-106.

Hanafusa et al., "A Robot Hand with Elastic Fingers and Its Application to Assembly Process," pp. 337-359, Robot Motion, Brady et al., MIT Press, Cambridge, MA, 1982.

Hansen, A. H., Childress, D. S., Miff, S. C., Gard, S. A., Mesplay, K. P., "The human ankle during walking: implication for the design of biomimetic ankle prosthesis," Journal of Biomechanics, vol. 37, No. 10, Oct. 2004, pp. 1467-1474.

Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.

Heglund, N., "A Simple Design for a Force-Plat to Measure Ground Reaction Forces," J. Exp. Biol., vol. 93, Aug. 1981, pp. 333-338.

Herr, H., et. al, "A model of scale effects in mammalian quadrupedal running," J Exp Biol 205 (Pt 7), Apr. 2002, pp. 959-967.

Herr, H. and Wilkenfeld A., "User-adaptive control of a magnetorheologicalprosthetic knee," Industrial Robot: An International Journal, vol. 30, No. 1, 2003, pp. 42-55.

Herr, H. and Popovic, M., "Angular momentum regulation in human walking," J. Exp. Biol., vol. 211, Feb. 2008, pp. 467-481.

Herr, H. and McMahon, T., "A trotting horse model," Int. J. Robotics Res., vol. 19, No. 6, Jun. 2000, pp. 566-581.

Heyn et al., "The Kinematice of the Swing Phase Obtained from Accelerometer and Gyroscope Measurements," 18$^{th}$ Annual International Conference of the IEEE Engineering in Medicine and Biology Society, Nov. 1996, Amsterdam, Netherlands, pp. 463-464.

Hill, V., "The heat of shortening and the dynamic constants of muscle," Proceedings of the Royal Society London B, vol. 126, No. 843, Oct. 1938, pp. 136-195.

Hirai, K., et al., "The development of Honda humanoid robot," Proceedings on IEEE/RSJ International Conference on Intelligent Robots and Systems, May 1998, Leuven, Belgium, pp. 1321-1326.

Hitt, J., R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom., Orlando, Fla., pp. 2939-2945, Sep. 2007.

Hof. A., et. al., "Calf muscle moment, work and efficiency in level walking; role of series elasticity," Journal of Biomechanics, vol. 16, No. 7, Sep. 1983, pp. 523-537.

Hofbaur, M. and Williams, B., "Hybrid Diagnosis with Unknown Behavioral Modes", Proceedings of the 13.sup.th International Workshop on Principles of Diagnosis (DX02), May 2002, pp. 1-10.

Hofbaur, M. and Williams, B., "Mode Estimation of Probabilistic Hybrid Systems", HSSC 2002, LNCS 2289, Mar. 25, 2002, pp. 253-266.

Hofmann, A., et. al., "A Sliding Controller for Bipedal Balancing Using Integrated Movement of Contact and Non-Contact Limbs," Proceedings of the IEEE/RSJ International Conference on Intelligent Robots and Systems, Sep. 2004, Sendai, Japan, pp. 1952-1959.

Hofmann, A., et. al., "Robust Execution of Bipedal Walking Tasks from Biomechanical Principles," Doctor of Philosophy at the Massachusetts Institute of Technology, Jan. 2006, 407 pages.

Hogan, N. (1976) A review of the methods of processing EMG for use as a proportional control signal. Biomedical Engineering. pp. 81-86.

Hogan, N., "Impedance Control: An Approach to Manipulation: Part I—Theory, " Journal of Dynamic Systems, Measurement , and Control, vol. 107, Mar. 1985, pp. 1-7.

Hollander, K. W., T. G. Sugar, and D. E. Herring, "Adjustable robotic tendon using a 'Jack Spring'.TM.," Proceedings on IEEE International Conference on Rehabilitation Robotics, Chicago, pp. 113-118, Jun. 28, 2005.

Howard, "Joint and Actuator Design for Enhanced Stability in Robotic Force Control," Ph.D. thesis, Massachusetts Inst. of Technology, Dept. of Aeronautics and Astronautics, Sep. 19, 1990.

Huang, H. and Chen. C., "Development of a myoelectric discrimination system for a multi-degree prosthetic hand," Proceeding of the 1999 IEEE International Conference on Robotics and Automation, May 1999, Detroit, MI, pp. 2392-2397.

Huang, Q., "Planning walking patterns for a biped robot," IEEE Transactions on Robotics and Automation, vol. 17, No. 3, Jun. 2001, pp. 280-289.

Hultborn, H., Spinal reflexes, mechanisms and concepts: from Eccles to Lundberg and beyond, Prog Neurobiol, vol. 78, Feb. 2006, pp. 215-232.

Ijspeert, A. J., 2008, "Central pattern generators for locomotion control in animals and robots: a review," Neural Netw, vol. 21, No. 4, May 2008, pp. 642-653.

Ijspeert, A., et. al., "From swimming to walking with a salamander robot driven by a spinal cord model," Science, vol. 315, No. 5817, Mar. 2007, pp. 1416-1420.

International Preliminary Search Report for PCT/US10/047279 mailed Mar. 15, 2012, 7 pages.

Ivashko, D., et. al, "Modeling the spinal cord neural circuitry controlling cat hindlimb movement during locomotion," Neurocomputing, vol. 52-54, Mar. 2003, pp. 621-629.

Johansson, J., et al., "A clinical comparison of variable damping and mechanically passive prosthetic knee devices," American Journal of Physical Medicine & Rehabilitation, vol. 84, No. 8, Aug. 2005, pp. 563-575.

Johnson, C. and Lorenz R., "Experimental identification of friction and its compensation in precise, position controlled mechanisms," IEEE Trans. on Industry Applications, vol. 28, No. 6, Dec. 1992, pp. 1392-1398.

Jonic S, et. al., "Three machine learning techniques for automatic determination of rules to control locomotion," IEEE Trans Biomed Eng, vol. 46, No. 3, Mar. 1999, pp. 300-310.

Kadaba, M., et. al., "Measurement of lower extremity kinematics during level walking," J. Orthop. Res., vol. 8, May 1990, pp. 383-392.

Kadaba, M., et. al., "Repeatability of kinematic, kinetic, and electromyographic data in normal adult gait," J. Orthop. Res., vol. 7, Nov. 1989, pp. 849-860.

Kajita, K., et. al., "Biped walking on a low friction floor," Proceedings of the 2004 IEEE/RSJ International Conference on Intelligent Robots and Systems, Oct. 2004, Sendai, Japan., pp. 3546-3551.

Kajita, S., et. al., "Resolved Momentum Control: Humanoid Motion Planning based on the Linear and Angular Momentum," Proceedings of the 2003 IEEE/RSJ International Conference on Intelligent Robots and Systems, Oct. 2003, Las Vegas, Nev., pp. 1644-1650.

Kajita, S., et. al., "A Hop towards Running Humanoid Biped," Proceedings of the 2004 IEEE International Conference on Robotics and Automation, Apr. 2004, New Orleans, La., pp. 629-635.

Kaneko, K., et al., "Humanoid robot HRP-2," Proc. IEEE Int. Conf. on Robotics and Automation, Apr. 2004, New Orleans, La., pp. 1083-1090.

Kapti, A. and Yucenur M., "Design and control of an active artificial knee joint," Mechanism and Machine Theory, vol. 41, Apr. 2006, pp. 1477-1485.

Katic, D. and Vukobratovic, M., "Survey of intelligent control techniques for humanoid robots," Journal of Intelligent and Robotics Systems, vol. 37, Jun. 2003, pp. 117-141.

Kerrigan, D, et. al., "A refined view of thedeterminants of gait: significance of heel rise," Arch. Phys. Med. Rehab., vol. 81, Aug. 2000, pp. 1077-1080.

Kerrigan, D, et. al., "Quantification of pelvic rotation as a determinant of gait," Arch. Phys. Med. Rehab., vol. 82, Feb. 2001, pp. 217-220.

Khatib, O., et. al., "Coordination and decentralized cooperation of multiple mobile manipulators," Journal of Robotic Systems, vol. 13, No. 11, Nov. 1996, pp. 755-764.

Khatib, O., et. al., "Whole body dynamic behavior and control of human-like robots," International Journal of Humanoid Robotics, vol. 1, No. 1, Mar. 2004, pp. 29-43.

Kidder, et al., "A System for the Analysis of Foot and Ankle Kinematics During Gait," IEEE Transactions on Rehabilitation Engineering, vol. 4, No. 1, Mar. 1996, pp. 25-32.

Kim, et al., "Realization of Dynamic Walking for the Humaniod Robot Platform KHR-1," Advanced Robotics, vol. 18, No. 7, May 2004, pp. 749-768.

Kirkwood C, et. al., "Automatic detection of gait events: a case study using inductive learning techniques.," J Biomed Eng, vol. 11, Nov. 1989, pp. 511-516.

Kitayama, I., Nakagawa N, Amemori K, "A microcomputer controlled intelligent A/K prosthesis," Proceedings of the 7th' World Congress of the International Society for Prosthetics and Orthotics, Chicago. Jun. 28, 1992.

Klute, G., et. al., "Mechanical properties of prosthetic limbs adapting to the patient," Journal of Rehabilitation Research and Development, vol. 38, No. 3, May 2001, pp. 299-307.

Koganezawa, K. and Kato, I., "Control aspects of artificial leg," IFAC Control Aspects of Biomedical Engineering, 1987, pp. 71-85.

Kondak, K. and Hommel, G., "Control and online computation of stable movement for biped robots," Proc. of the 2003 IEEE/RSJ International Conference on Intelligent Robots and Systems (IROS), Oct. 2003, Las Vegas, Nev., pp. 874-879.

Kostov A., et. al., "Machine learning in control of functional electrical stimulation (FES) systems for locomotion," IEEE Trans on Biomed Eng, vol. 42, No. 6, Jun. 1995, pp. 541-551.

Kuo, A., "A simple model of bipedal walking predicts the preferred speed-step length relationship," Journal of Biomechanical Engineering, vol. 123, Jun. 2001, pp. 264-269.

Kuo, A., "Energetics of actively powered locomotion using the simplest walking model," Journal of Biomechanical Engineering, vol. 124, Feb. 2002, pp. 113-120.

LaFortune, "Three-Dimensional Acceleration of the Tibia During Walking and Running," J. Biomechanics, vol. 24, No. 10, 1991, pp. 877-886.

LeBlanc, M. and Dapena, J., "Generation and transfer of angular momentum in the javelin throw," Presented at the 20th annual meeting of the American Society of Biomechanics, Oct. 1996, Atlanta, Ga., pp. 17-19.

Liu, X., Low, K. H., Yu, H. Y., Sep. 2004 'Development of a Lower Extremity Exoskeleton for Human performance Enhancement', IEEE Conf. On Intelligent Robots and Systems, Sendai, Japan.

Light, et. al., Skeletal Transients on Heel Strike in Normal Walking With Different Footwear. J. Biomechanics vol. 13, pp. 477-480.

Lloyd R. and Cooke C., "Kinetic changes associated with load carriage using two rucksack designs," Ergonomics, vol. 43, No. 9, Sep. 2000, pp. 1331-1341.

Luinge, "Inertial Sensing of Human Movement," Twente University Press, ISBN 9036518237, 2002, pp. 1-80.

Lundberg, A., Oct. 19, 1968. Reflex control of stepping. In: The Nansen memorial lecture V, Oslo: Universitetsforlaget, 5-42.

Macfarlane, P., "Gait comparisons for below-knee amputees using a flex-foot versus a conventional prosthetic foot," Journal of Prosthetics & Orthotics, vol. 3, No. 4, Summer, 1991, pp. 150-161.

Maganaris, C., "Force-length characteristics of in vivo human skeletal muscle," Acta Physiol. Scand., vol. 172, Aug. 2001, pp. 279-285.

Maganaris, C., "Force-length characteristics of the in vivo human gastrocnemius muscle," Clin. Anat., vol. 16, May 2003, pp. 215-223.

Martens, W.L.J., "Exploring the Information Content and Some Applications of Body Mounted Piezo-Resistive Accelerometers," in: P.H. Veltink and R.C. van Lummel (eds.), Dynamic Analysis using Body Fixed Sensors, ISBN 90-9007328-0, 1994, pp. 8-11.

Maufroy, C., Towards a general neural controller for quadrupedal locomotion, Neural Netw, vol. 21, No. 4, Apr. 2008, pp. 667-681.

Mayagoitia R., et al., "Accelerometer and rate gyroscope measurement of kinematics: an inexpensive alternative to optical motion analysis systems," Journal of Biomechanics, vol. 35, Apr. 2002, pp. 537-542.

McGeer T., "Passive Dynamic Walking," International Journal of Robotics, vol. 9, No. 2, May 1988, pp. 62-82.

McGeer, T., "Principles of walking and running," Advances in Comparative and Environmental Physiology, vol. 11, Ch. 4, Apr. 1992, pp. 113-139.

McIntosh, A., et. al., "Gait dynamics on an inclined walkway," Journal of Biomechanics, vol. 39, Sep. 2005, pp. 2491-2502.

McMahon, T., "The mechanics of running: how does stiffness couple with speed?," J. of Biomecb., vol. 23, 1990, pp. 65-78.

McMahon, T., et. al., "Groucho Running," Journal of Applied Physiology, vol. 62, No. 6, Jun. 1987, pp. 2326-2337.

Minassian, K., et. al., "Human lumbar cord circuitries can be activated by extrinsic tonic input to generate locomotor-like activity," Hum. Mov. Sci., vol. 26, Mar. 2007, pp. 275-295.

Mochon, S., et. al., "Ballistic walking," Journal of Biomechanics, vol. 13, Dec. 1980, pp. 49-57.

Molen, N., "Energy/speed relation of below-knee amputees walking on motor-driven treadmill," Int. Z. Angew. Physio, vol. 31, Mar. 1973, pp. 173.

Morris, "Accelerometry—A Technique for the Measurement of Human Body Movements," J. Biomechanics, vol. 6, Nov. 1973, pp. 729-736.

Muraoka, T., et. al, "Muscle fiber and tendon length changes in the human vastus lateralis during slow pedaling," J. Appl. Physiol., vol. 91, Nov. 2001, pp. 2035-2040.

Nakagawa A., "Intelligent Knee Mechanism and the Possibility to Apply the Principle to the Other Joints," Proceedings of the 20th Annual International Conference of the IEEE Engineering in Medicine and Biology Society, Vo. 20, No. 5, Oct. 1998, pp. 2282-2287.

Neal R. and Hinton G., "A view of the EM algorithm that justifies incremental, sparse, and other variants," in Michael I. Jordan (editor), Learning in Graphical Models, 1999, Cambridge, MA, pp. 1-14.

Ng, et al., "Fuzzy Model Identification for Classification of Gait Events in Paraplegics," IEEE Transactions on Fuzzy Systems, vol. 5, No. 4, Nov. 1997, pp. 536-544.

Nielsen, D., et. al., "Comparison of energy cost and gait efficiency during ambulation in below-knee amputees using different prosthetic feet—a preliminary report," Journal of Prosthetics & Orthotics, vol. 1, No. 1, 1989, pp. 24-29.

Ogihara, N. and Yama7aki, N., "Generation of human bipedal locomotion by a bio-mimetic neuro-musculo-skeletal model," Biol Cybern, vol. 84, No. 1, Jan. 2001, pp. 1-11.

Palmer, M., "Sagittal plane characterization of normal human ankle function across a range of walking gait speeds," Masters Thesis, MIT, Feb. 2002, Cambridge, MA, pp. 1-71.

Paluska, D., and Herr, H., "The effect of series elasticity on actuator power and work output: implications for robotic and prosthetic joint design," Robotics and Autonomous Systems, vol. 54, Jun. 2006, pp. 667-673.

Paluska, D. and Herr, H., "Series Elasticity and Actuator Power Output," Proceedings of the 2006 IEEE International Conference on Robotics and Automation, May 2006, Orlando, FL, pp. 1830-1833.

Pang, M., et. al., "The initiation of the swing phase in human infant stepping: importance of hip position and leg loading," J Physiol, vol. 528, No. 2, Oct. 2000, pp. 389-404.

Pasch, K. A., and W. P. Seering, "On the drive systems for high performance machines," AMSE J. Mechanisms, Transmissions, and Automation in Design vol. 106, pp. 102-108, Mar. 1984.

Paul, C., et. al., "Development of a human neuro-musculo-skeletal model for investigation of spinal cord injury," Biol Cybern, vol. 93, No. 3, Aug. 2005, pp. 153-170.

Pearson, K., "Generating the walking gait: role of sensory feedback," Prog Brain Res, vol. 143, 2004, pp. 123-129.

Pearson, K., et. al., "Assessing sensory function in locomotor systems using neuro-mechanical simulations," Trends Neurosci, vol. 29, No. 11, Nov. 2006, pp. 625-631.

Perry, Gait Analysis: Normal and Pathological Function, New Jersey: SLACK Inc.; 1992, Book Review, 1 page.

Perry, J. and S. Shanfield, "Efficiency of dynamic elastic response prosthetic feet," Journal of Rehabilitation Research and Development, vol. 30, No. 1, 1993 pp. 137-143.

Petrofshy et al., "Feedback Control System for Walking in Man," Comput. Biol. Med., vol. 14, No. 2, Mar. 1984, pp. 135-149.

Pfeffer et al., "Experiments with a Dual-Armed, Cooperative, Flexible-Drivetrain Robot System," Proc. 1993 IEEE Int. Conf. on Robotics & Automation, vol. 3, pp. 601-608, May 5, 1993.

Popovic D., et al., "Control Aspects of Active Above-Knee Prosthesis," Int. Journal Man-Machine Studies, (1991) 35, pp. 751-767.

Popovic, D., "Control of Movement for the Physically Disabled," Springer-Verlag London Limited, May 2000, pp. 270-302.

Popovic, M. and Herr, H., "Global Motion Control and Support Base Planning," Proceedings of the IEEE/RSJ International Conference on Intelligent Robots and Systems, Aug. 2005, Alberta, Canada, pp. 1-8.

Popovic, M., et. al., "Angular Momentum Regulation during human walking: Biomechanics and Control," Proceedings of the 2004 IEEE International Conference on Robotics and Automation, Apr. 2004, New Orleans, LA, pp. 2405-2411.

Popovic, M., et. al., "Zero spin angular momentum control: definition and applicability," Proceedings of the IEEE-RAS/RSJ International Conference on Humanoid Robots, Nov. 2004, Los Angeles, CA, pp. 1-16.

Popovic, M., "Angular Momentum Primitives for Human Walking: Biomechanics and Control," Proc. of the 2004 IEEE/RSJ International Conference on Intelligent Robots and Systems, Sep. 2004, Sendai, Japan., pp. 1685-1691.

Popovic, et al., "Gait Identification and Recognition Sensor," Proceedings of 6th Vienna International Workshop on Functional Electrostimulation, Sep. 1998, pp. 1-4.

Popovic, M., et. al., "Ground Reference Points in Legged Locomotion: Definitions, Biological Trajectories and Control Implications," International Journal of Robotics Research, Dec. 2006, pp. 79-104.

Popovic, M.B., W. Gu and H. Herr, "Conservation of Angular Momentum in Human Movement," MIT AI Laboratory-Research Abstracts, Sep. 2002. pp. 231-232, 2002.

Pratt, G. and Williamson M., "Series elastic actuators," Proceedings on IEEE/RSJ International Conference on Intelligent Robots and Systems, Jan. 1995, Pittsburgh, PA, pp. 399-406.

Pratt, G., "Legged Robots: What's New Since Raibert," IEEE Robotics and Automation Magazine, Research Perspectives, Sep. 2000, pp. 15-19.

Pratt, G., "Low Impedance Walking Robots," Integ. and Comp. Biol., vol. 42, Feb. 2002, pp. 174-181.

Pratt, J., et. al., "The RoboKnee: An Exoskeleton for Enhancing Strength and Endurance During Walking", IEEE Conf. on Robotics and Automation, Apr. 2004, New Orleans, LA, pp. 2430-2435.

Prochazka, A., et. al., "Positive force feedback control of muscles," J. of Neuro-phys., vol. 77, Jun. 1997, pp. 3226-3236.

Prochazka, A., et. al., "Sensory control of locomotion: reflexes versus higher-level control," Adv Exp Med Biol, vol. 508, 2002, pp. 357-367.

Prochazka, A. and Yakovenko, S., "The neuromechanical tuning hypothesis," Prog Brain Res, vol. 165, Oct. 2007, pp. 255-265.

Raibert, M., "Legged Robots that Balance," The MIT Press, Nov. 1986, Cambridge, MA, p. 89.

Rassier, D., et. al., "Length dependence of active force production in skeletal muscle," Journal of Applied Physiology, vol. 86, Issue 5, May 1999, pp. 1455-1457.

Riener, R., et. al., "Stair ascent and descent at different inclinations," Gait Posture, vol. 15, Feb. 2002, pp. 32-44.

Reitman, et. al., Gait analysis in prosthetics: opinions, ideas and conclusions, Prosthetics and Orthotics International, 2002, 26, 50-57.

Robinson, D., "Series elastic actuator development for a biomimetic walking robot," Proceedings of IEEE/ASME International Conference on Advanced Intelligent Mechatronics, Sep. 1999, pp. 561-568.

Robinson, D., "Design and an analysis of series elasticity in closed-loop actuator force control," Ph.D. Thesis, MIT, Jun. 2000, Cambridge, MA, pp. 1-123.

Rosen, J., et al., "A myosignal-based powered exoskeleton system," IEEE Transactions on Systems, Man, and Cybernetics—Part A: Systems and Humans, vol. 31, No. 3, May 2001, pp. 210-222.

Ruina, A., et. al., "A collisional model of the energetic cost of support work qualitatively explains leg sequencing in walking and galloping, pseudo-elastic leg behavior in running and the walk-to-run transition," Journal of Theoretical Biology, vol. 237, Issue 2, Jun. 2005, pp. 170-192.

Rybak, I., et. al., "Modelling spinal circuitry involved in locomotor pattern generation: insights from deletions during fictive locomotion," J Physiol, vol. 577 (Pt 2), Dec. 2001, 617-639.

Sanderson, D., et. al., "Lower extremity kinematic and kinetic adaptations in unilateral below-knee amputees during walking," Gait and Posture, vol. 6, No. 2, Oct. 1997, pp. 126-136.

Sanger, T., "Human arm movements described by a low-dimensional superposition of principal component," Journal of NeuroScience, vol. 20, No. 3, Feb. 2000, pp. 1066-1072.

Saranli, U., "RHex: A simple and highly mobile hexapod robot," Int. Jour. Rob. Res., vol. 20, No. 7, Jul. 2001, pp. 616-631.

Sarrigeorgidis K. and Kyriakopoulos K., "Motion control of the N.T.U.A. robotic snamek on a planar surface," Proc. of the 1998 IEEE International Conference on Robotics and Automation, May 1998, pp. 2977-2982.

Schaal, S. and Atkeson, C., "Constructive incremental learning from only local information," Neural Computation, vol. 10, No. 8, Nov. 1998, pp. 2047-2084.

Schaal, S., "Is imitation learning the route to humanoid robots?" Trends in Cognitive Sciences, vol. 3, Jun. 1999, pp. 233-242.

Scott, S. and Winter, D., "Biomechanical model of the human foot: kinematics and kinetics during the stance phase of walking," J. Biomech., vol. 26, No. 9, Sep. 1993, 1091-1104.

Sentis, L. and O. Khatib, "Task-Oriented Control of Humanoid Robots Through Prioritization," IEEE-RAS/RSJ International Conference on Humanoid Robots, Nov. 2004, Santa Monica, CA, pp. 1-16.

Seyfarth, A., et. al., "A movement criterion for running," J. of Biomech., vol. 35, May 2002, pp. 649-655.

Seyfarth, A., "Swing-leg retraction: a simple control model for stable running," J. Exp. Biol., vol. 206, Aug. 2003, pp. 2547-2555.

Seyfarth, A., et. al., "Stable operation of an elastic three-segmented leg," Biol.Cybern., vol. 84, 2001, pp. 365-382.

Simon F., et. al, "Convergent force fields organized in the frog's spinal cord," Journal of NeuroScience, vol. 13, No. 2, Feb. 1993, pp. 467-491.

Sinkjaer, T., et. al., "Major role for sensory feedback in soleus EMG activity in the stance phase of walking in man," J Physiol, vol. 523, No. 3, Mar. 2000, 817-827.

Skinner, H. and Effeney D., "Gait analysis in amputees," Am J Phys Med, vol. 64, Apr. 1985, pp. 82-89.

Smidt et al., "An Automated Accelerometry System for Gait Analysis," J. Biomechanics, vol. 10, 1977, pp. 367-375.

Srinivasan, M., "Energetics of legged locomotion: Why is total metabolic cost proportional to the cost of stance work," Proc. on ISB XXth Congress and the American Society of Biomechanics Annual Meeting, Jul. 2003, Cleveland, OH, pp. 829.

Stepien, J., et al., "Activity Levels Among Lower-Limb Amputees: Self-Report Versus Step Activity Monitor," Arch. Phys. Med. Rehabil., vol. 88, No. 7, Jul. 2007, pp. 896-900.

Sugano et al., "Force Control of the Robot Finger Joint equipped with Mechanical Compliance Adjuster," Proc. of the 1992 IEEE/RSJ Int. Conf. on Intell. Robots & Sys., Jul. 1992, pp. 2005-2013.

Sugihara, T., et. al., "Realtime Humanoid Motion Generation through ZMP Manipulation based on Inverted Pendulum Control," Proceedings of the 2002 IEEE International Conference on Robotics and Automation, May 2002, Washington, DC, pp. 1404-1409.

Sup, F., "Design and Control of a Powered Transfemoral Prosthesis," The International Journal of Robotics Research, vol. 27, No. 2, Feb. 2008, pp. 263-273.

Taga, G., "A model of the neuro-musculo-skeletal system for human locomotion," Biol. Cybern., vol. 73, No. 2, Jul. 1995, pp. 97-111.

Takayuki "Biped Locomotion using Multiple Link Virtual Inverted Pendulum Model," Publication of Electronics Information and Systems Society, vol. 120, No. 2, Feb. 2000, 8 pages.

Thoroughman, K. and R. Shadmehr, "Learning of action through adaptive combination of motor primitives," Nature, vol. 407, Oct. 2000, pp. 742-747.

Tomovic R. et al., "A Finite State Approach to the Synthesis of Bioengineering Control Systems," IEEE Transations on Human Factors in Electronics, vol. 7, No. 2, Jun. 1966, pp. 65-69.

Tong, et al., "A Practical Gait Analysis System Using Gyroscopes," Medical Engineering & Physics, vol. 21, Mar. 1999, pp. 87-94.

Turker, K., "Electromyography: some methodological problems and issues," Physical Therapy, vol. 73, No. 10, Oct. 1993, pp. 698-710.

van den Bogert, A., "Exotendons for assistance of human locomotion," Biomedical Engineering Online, Oct. 2003, pp. 1-8.

van den Bogert, et al. "A Method for Inverse Dynamic Analysis Using Accelerometry," Journal Biomechanics, vol. 29, No. 7, 1996, pp. 949-954.

Veltink P., et al., "The Feasibility of Posture and Movement Detection by Accelerometry," D-7803-1377-I/93, IEEE, Oct. 1993, pp. 1230-1231.

Vukobratovic M. and Juricic, D., "Contributions to the synthesis of biped gait," IEEE Transactions on Biomedical Engineering, vol. BME-16, No. 1, Jan. 1969, pp. 1-6.

Vukobratovic M. and Stepanenko J., "Mathematical models of general anthropomorphic systems," Mathematical Biosciences, vol. 17, Aug. 1973, pp. 191-242.

Walsh, C., "Biomimetic Design of an Under-Actuated Leg Exoskeleton for Load-Carrying Augmentation," Masters Thesis, MIT, Feb. 2006, pp. 1-94.

Waters, RL., "Energy cost of walking amputees: the influence of level of amputation," J Bone Joint Surg., vol. 58, No. 1, Jan. 1976, pp. 42-46.

Wilkenfeld, A. J., "Biologically inspired auto adaptive control of a knee prosthesis," Ph.D. Thesis, Massachusetts Institute of Technology, Oct. 23, 2000.

Wilkenfeld, A., "An Auto-Adaptive External Knee Prosthesis," Artificial Intelligence Laboratory, MIT, Sep. 2000, Cambridge, MA, pp. 1-3.

Williamson, M., "Series Elastic Actuators," Artificial Intelligence Laboratory, MIT, Jan. 1995, Cambridge, MA, pp. 1-74.

Willemsen A., et al., "Automatic Stance-Swing Phase Detection from Accelerometer Data for Peroneal Nerve Stimulation," IEEE Transactions on Human Factors in Electronics, vol. 37, No. 12, Dec. 1990, pp. 1201-1208.

Willemsen A., et al., "Real-Time Gait Assessment Utilizing a New Way of Accelerometry," Journal of Biomechanics, vol. 23, No. 8, 1990, pp. 859-863.

Williams, B., "Mode Estimation of Model-based Programs: Monitoring Systems with Complex Behavior," Proceedings of the International Joint Conference on Artificial Intelligence, Aug. 2001, Seattle, WA, pp. 1-7.

Winter, D. and Sienko S., "Biomechanics of below-knee amputee gait," Journal of Biomechanics, vol. 21, No. 5, Aug. 1988, pp. 361-367.

Winter, D. A, "Energy generation and absorption at the ankle and knee during fast, natural, and slow cadences," Clinical Orthopedics and Related Research, vol. 175, May 1983, pp. 147-154.

Winter, D, and Robertson D., "Joint torque and energy patterns in normal gait," Biol. Cybem., vol. 29, May 1978, pp. 137-142.

Wisse, M., "Essentials of Dynamic Walking, Analysis and Design of two-legged robots," Ph.D. Thesis, Technical University of Delft, 2004, pp. 1-195.

Woodward et al., "Skeletal Accelerations measured during different Exercises," Proceedings of the Institution of Mechanical Engineers, Part H: Journal of Engineering in Medicine, vol. 207, Jun. 1993, pp. 79-85.

Wu, The Study of Kinematic Transients in Locomotion Using the Integrated Kinematic Sensor, IEEE Transactions on Rehabilitation Engineering, vol. 4, No. 3, Sep. 1996, p. 193-200.

Yakovenko, S., et. al., "Contribution of stretch reflexes to locomotor control: a modeling study," Biol Cybern, vol. 90, No. 2, Jan. 2004, pp. 146-155.

Yun X., "Dynamic state feedback control of constrained robot manipulators," Proc. of the 27th conference on Decision and Control, Dec. 1988, pp. 622-626.

Zlatnik, D., et. al., "Finite-state control of a trans-femoral prosthesis," IEEE Trans. on Control System Technology, vol. 10, No. 3, May 2002, pp. 408-420.

Hogan, N., "Impedance Control: An Approach to Manipulation: Part I—Theory." Journal of Dynamic Systems, Measurement, and Control, vol. 107, Mar. 1985, pp. 1-7.

Li, C., et al. (2006) Research and development of the intelligently-controlled prosthetic ankle joint. Proc. of IEEE Int. Conf. on Mechatronics and Automation. Luoyang, China, pp. 1114-1119.

McFadyen, B. and Winter, D., "An integrated biomechanical analysis of normal stair ascent and descent," Journal of Biomechanics, vol. 21, No. 9, 1988, Great Britain, pp. 733-744.

Oda, T, Kanehisa, et al., 2005, "In vivo lenth-force relationships on muscle fiver and muscle tendon complex in the tibialis anterior muscle." Int. J. Sport and Health Sciences 3, 245-252.

International Search Report and Written Opinion for PCT/US2011/031105 mailed Oct. 11, 2011 (17 pages).

Blaya, J.A., and Herr, H., "Adaptive Control of a Variable-Impedance Ankle-Foot Orthosis to Assist Drop Foot Gait," Artificial Intelligence Lab and Harvard—MIT Division Health Sciences and Technology, Boston, MA, vol. 12, No. 1, Mar. 2004, 30 pages.

Blaya, J.A., et al., "Active Ankle Foot Orthoses (AAFO)," http://www.ai.mit.edu. Artificial Intelligence Laboratory, Massachusetts Institute of Technology, Cambridge, Massachusetts, 2001, 3 pages.

Drake, C., "Foot & Ankle Splints or Orthoses," HemiHelp Information Sheet, London, United Kingdom, www.hemihelp.org.uk/leaflets/hbleaflets90.htm, Jun. 2003, pp. 1-3.

Klute, et al., "Variable Stiffness Prosthesis for Transtibial Amputees," Dept of Veteran Affairs, 2004, Seattle, WA USA, 2 pages.

Bouten et al., Assessment of energy expenditure for physical activity using a triaxial accelerometer. Med Sci Sports Exerc. Dec. 1994;26(12):1516-23.

Bouten, A Triaxial Accelerometer and Portable Data Processing Unit for the Assessment of Daily Physical Activity, IEEE Transactions on Biomedical Engineering, vol. 44, No. 3, Mar. 1997, pp. 136-147.

Colgate, The control of dynamically interacting systems. MIT. Aug. 1988. 1-19.

Davids et al., Disorders of Bone and Mineral Metabolism. Book reviews. J Ped Orthopaedics. 1992;12(6):815.

Fisekovic et al., New controller for functional electrical stimulation systems, Medical Engineering & Physics vol. 23, 2001, pp. 391-399.

Foerster et al., Detection of posture and motion by accelerometry a validation study in ambulatory monitoring, Computer in Human Behavior, 1999, pp. 571-583.

Foxlin et al., Miniature 6-DOF inertial system for tracking HMDs, In SPIE vol. 3362, Helmet and Head-Mounted Displays III. AeroSense 98, Orlando, FL, Apr. 13-14, 1998, 15 pages.

Giszter et al., Convergent force fields organized in the frog's spinal cord. J Neurosci. Feb. 1993;13(2):467-91.

Hashimoto et al., An instrumented compliant wrist using a parallel mechanism, Japan/USA Symposium on Flexible Automation, vol. 1, pp. 741-744, ASME, 1992.

Herr, New Horizons for Orthotic and Prosthetic Technology: Artificial Muscle for Ambulation MIT Media Laboratory. 2004:1-9.

Hogan, N and Buerger S., Impedance and Interaction Control, Robotics and Automation Handbook, CRC Press, Jun. 2004, pp. 19.1-19.24.

Isakower, Design Charts for Torsional Properties of Non-circular Shafts, Technical Report ARMID-TR-78001, ARRADCOM, MISD, DRDAR-MSA, Dover,NJ, Nov. 1978.

Lee et al., activity and Location recognition Using Wearable Sensors, Pervasive Computing, Jul.-Sep. 2002, pp. 24-32.

McFadyen et al., An integrated biomechanical analysis of normal stair ascent and descent. J Biomech. 1988;21(9):733-44.

Moe-Nilssen, A new method for evaluating motor control in gait under real-life environmental.conditions, Part 2: Gait analysis, Clinical biomechanics, vol. 13, 1998, pp. 328-335.

Popovic, M. and Herr, H., Global Motion Control and Support Base Planning, Proceedings of the IEEE/RSJ International Conference on Intelligent Robots and Systems, Aug. 2005, Alberta, Canada, pp. 1-8.

Rybak et al., Modelling spinal circuitry involved in locomotor pattern generation: insights from the effects of afferent stimulation. J Physiol. Dec. 1, 2006;577(Pt 2):641-58. Epub Sep. 28, 2006.

Sekine et al., Classification of waist-acceleration signals in a continuous walking record, Medical Engineering & Physics, vol. 22, 2000, pp. 285-291.

Sin et al., Significance of non-level walking on transtibial prosthesis fitting with particular reference to the effects of anterior-posterior alignment, Journal of Rehabilitation Research and Development, vol. 38, No. 1, Jan./Feb. 2001, p. 1-6.

Tong et al., Virtual artificial sensor technique for functional electricial stimulation, Medical Engineering & Physics, vol. 20, 1998, pp. 458-468.

van der Kooij et al., A multisensory integration model of human stance control, Biological Cybernetics, 1999, pp. 299-308.

Veltink, Dection of Static and Dynamic Activities Using Uniaxial Accelerometers, IEEE Transactions on Biomedical Engineering, vol. 4. No. 4, Dec. 1996, pp. 375-385.

\* cited by examiner

External Prosthesis, Robotic Limb, or Orthothosis in Heel Strike to Toe-Off Walking Sequence Prosthetic Mechanisms Designed to Power Plantar-flex Catapult Leg Prosthesis for Walking, Running, and Jumping Catapult Leg Prosthesis for Walking, Running, and Jumping External, Bi-articular Transfemoral Prosthesis, Robotic Limb, or Orthotic Brace in Heel-Strike to Toe-Off Walking Sequence External, Bi-articularTtransfemoral Prosthesis in Heel-Strike to Toe-Off Walking Sequence Variable Spring-Rate Joint Low-Profile Prosthetic Foot Example Prosthetic Ankle/Foot Variable-Spring-Rate Multiple-Pneumatic-Chamber and Energy Transfer System.

Prosthetic Ankle-Foot

Prior-Art Prosthetic Ankle-Foot

Variable Stiffness Spring for an External Prosthesis

VARIABLE MECHANICAL-IMPEDANCE ARTIFICIAL LEGS

CROSS-REFERENCE TO RELATED APPLICATIONS

This application is a continuation of U.S. application Ser. No. 10/613,499, filed on Jul. 3, 2003, which claims priority to U.S. Application Ser. No. 60/395,938, filed on Jul. 15, 2002, and incorporates by reference those applications in their entirety and claims priority thereto.

FIELD OF THE INVENTION

The invention relates generally to the fields of legged robotics, orthotic leg devices and prosthetic leg joints, and more specifically to artificial limbs with time-variable mechanical parameters.

BACKGROUND

Prosthetic limbs have come a long way since the days of simple wooden "peg legs". Today, amputee men running on a prosthetic leg can beat race times of the best unimpaired women runners. It is believed that new advances in prosthetic limbs (such as those embodied in the present invention) will soon lead to amputees being able to out-perform the best unimpaired athletes of the same sex in sports such as running. It is an object of the present invention to advance the state of prosthetic limbs to a new level, providing increased athletic performance, increased control, and reduced body strain. It is a further object of the present invention to provide essential elements needed for making prosthetic limbs that more accurately mimic the mechanical behavior of healthy human limbs.

Description of Normal, Level-Ground Walking:

In order to establish terminology used in this document, the basic walking progression from heel strike to toe off is first explained. There are three distinct phases to a walking stance-period as depicted in FIG. 1 with heel-toe sequence 1 through 7.

Saggital Plane Knee Phases
1. Beginning with heel strike, the stance knee begins to flex slightly (Sequence 1-3). This flexion allows for shock absorption upon impact as well as keeping the body's center of gravity at a more constant vertical level throughout stance.
2. After maximum flexion is reached in the stance knee, the joint begins to extend again, until full extension is reached (Sequence 3-5).
3. During late stance, the knee of the supporting leg begins to flex again in preparation for the swing phase (Sequence 5-7). This is referred to in the literature as "knee break". At this time, the adjacent foot strikes the ground and the body is in "double support mode" (that is to say, both legs are supporting body weight).

Saggital Plane Ankle Phases
1. Beginning with heel strike, the ankle undergoes a controlled plantar-flexion phase where the foot rotates towards the ground until the forefoot makes contact (Sequence 1-2).
2. After controlled plantar-flexion, the ankle undergoes a controlled dorsi-flexion phase where the tibia rotates forwardly while the foot remains in contact with the ground (Sequence 2-5).
3. During late stance, the ankle undergoes a powered plantar-flexion phase where the forefoot presses against the ground raising the heel from the ground (Sequence 5-7). This final phase of walking delivers a maximal level of mechanical power to the walking step to slow the fall of the body prior to heel strike of the adjacent, forwardly positioned leg.

The development of artificial leg systems that exhibit natural knee and ankle movements has been a long standing goal for designers of legged robots, prostheses and orthoses. In recent years, significant progress has been made in this area. The current state-of-the-art in prosthetic knee technology, the Otto Bock C-Leg, enables amputees to walk with early stance knee flexion and extension, and the state-of-the-art in ankle-foot systems (such as the Ossur Flex-Foot) allow for ankle controlled plantar-flexion and dorsi-flexion. Although these systems restore a high level of functionality to leg amputees, they nonetheless fail to restore normal levels of ankle powered plantar-flexion, a movement considered important not only for biological realism but also for walking economy. In FIG. 2, ankle power data are shown for ten normal subjects walking at four walking speeds from slow (½ m/sec) to fast (1.8 m/sec). As walking speed increases, both positive mechanical work and peak mechanical power output increase dramatically. Many ankle-foot systems, most notably the Flex-Foot, employ springs that store and release energy during each walking step. Although some power plantar-flexion is possible with these elastic systems, normal biological levels are not possible. In addition to power limitations, the flex-foot also does not change stiffness in response to disturbances. The human ankle-foot system has been observed to change stiffness in response to forward speed variation and ground irregularities. In FIG. 3, data are shown for a normal subject walking at three speeds, showing that as speed increases ankle stiffness during controlled plantar-flexion increases.

Artificial legs with a mechanical impedance that can be modeled as a spring in parallel with a damper are known in the art. Some prostheses with non-linear spring rates or variable damping rates are also known in the art. Unfortunately, any simple linear or non-linear spring action cannot adequately mimic a natural limb that puts out positive power during part of the gait cycle. A simple non-linear spring function is monotonic, and the force vs. displacement function is the same while loading the spring as while unloading the spring. It is an object of the present invention to provide actively electronically controlled prosthetic limbs which improve significantly on the performance of artificial legs known in the art, and which require minimal power from batteries and the like. It is a further object of the present invention to provide advanced electronically-controlled artificial legs which still function reasonably well should the active control function fail (for instance due to power to the electronics of the limb being lost). Still further, it is an object of the present invention to provide artificial legs capable of delivering power at places in the gait cycle where a normal biological ankle delivers power. And finally, it is an object of the present invention to provide prosthetic legs with a controlled mechanical impedance and the ability to deliver power, while minimizing the inertial moment of the limb about the point where it attaches to the residual biological limb.

During use, biological limbs can be modeled as a variable spring-rate spring in parallel with a variable damping-rate damper in parallel with a variable-power-output forcing function (as shown in FIG. 4a). In some activities, natural human limbs act mostly as spring-damper combinations. One example of such an activity is a slow walk. When walking slowly, a person's lower legs (foot and ankle system) act mostly as a system of springs and dampers. As walking speed increases, the energy-per-step put out by the muscles in the lower leg increases. This is supported by the data in FIG. 2.

Muscle tissue can be controlled through nerve impulses to provide variable spring rate, variable damping rate, and variable forcing function. It is an objective of the present invention to better emulate the wide range of controllability of damping rate, spring rate, and forcing function provided by human muscles, and in some cases to provide combination of these functions which are outside the range of natural muscles.

SUMMARY OF THE INVENTION

There are two major classes of embodiments of the present invention. The first major class provides for actively controlled passive mechanical parameters (actively controlled spring rate and damping rate). This major class of embodiments will be referred to as variable-stiffness embodiments. Three sub-classes of variable-stiffness embodiments are disclosed:
1) Multiple parallel interlockable springs.
2) Variable mechanical advantage.
3) Pressure-variable pneumatics.

The second major class of embodiments of the present invention allows for the controlled storage and release of mechanical energy within a gait cycle according to any arbitrary function, including functions not available through simple nonlinear springs. Within this second major class of embodiments, energy can be stored and released at rates which are variable under active control. Thus for a given joint, the force vs. displacement function is not constrained to be monotonic or single-valued. Within this class of embodiments, energy (from either muscle or a separate on-board power source) can be stored and released along arbitrarily defined functions of joint angular or linear displacement, force, etc. This major subclass of embodiments shall be referred to herein as energy transfer embodiments. Two subclasses of energy transfer embodiments are disclosed:
1) Bi-articular embodiments (which transfer energy from a proximal joint to a distal joint to mimic the presence of a missing joint).
2) Catapult embodiments (which store energy from a power source over one span of time and release it over another span of time to aid locomotion).

The present invention makes possible prostheses that have mechanical impedance components (damping and spring rate) and power output components that are actively controllable as functions of joint position, angular velocity, and phase of gait. When used in a prosthetic leg, the present invention makes possible control of mechanical parameters as a function of how fast the user is walking or running, and as a function of where within a particular step the prosthetic leg is operating.

It is often necessary to apply positive mechanical power in running shoes or in orthotic and prosthetic (O&P) leg joints to increase locomotory speed, to jump higher, or to produce a more natural walking or running gait. For example, when walking at moderate to high speeds, the ankle generates mechanical power to propel the lower leg upwards and forwards during swing phase initiation. In FIG. 2, data are shown for ten normal subjects showing that the ankle delivers more energy during a single step than it absorbs, especially for moderate to fast walking speeds.

Two catapult embodiments of the present invention are described in which elastic strain energy is stored during a walking, running or jumping phase and later used to power joint movements. In a first embodiment, catapult systems are described in which storage and release of stored elastic energy occurs without delay. In a second embodiment, elastic strain energy is stored and held for some time period before release. In each Embodiment, mechanism architecture, sensing and control systems are described for shoe and O&P leg devices. Although just a few devices are described herein, it is to be understood that the principles could be used for a wide variety of applications within the fields of human-machine systems or legged robots. Examples of these first and second catapult embodiments are shown in FIGS. 4 through 6.

One bi-articular embodiment of the invention described herein comprises a system of knee-ankle springs and clutches that afford a transfer of energy from hip muscle extensor work to artificial ankle work to power late stance plantar-flexion. Since the energy for ankle plantar-flexion originates from muscle activity about the hip, a motor and power supply need not be placed at the ankle, lowering the total mass of the knee-ankle prosthesis and consequently the metabolic cost associated with accelerating the legs in walking. Examples of these embodiments are shown in FIGS. 7 and 8.

Several variable-stiffness embodiments are described herein in which variable spring-rate structures are constructed by varying the length of a moment arm which attaches to a spring element about a pivot axis, thus providing a variable rotational spring rate about the pivot axis. Examples of such embodiments are depicted in FIGS. 9 through 11. In a preferred embodiment, variations in the length of the moment arm are made under microprocessor control at times of zero load, to minimize power consumed in the active control system.

Variable-stiffness embodiments of the present invention employing multiple interlockable parallel spring elements are depicted in FIGS. 12 through 14. In FIGS. 12a and 12b, multiple parallel elastic leaf spring elements undergo paired interlocking at pre-set joint flexures or under microprocessor control. This embodiment makes possible arbitrary piecewise-linear approximations to non-linear spring functions (such as function 624 in FIG. 12d). A pneumatic embodiment which can be configured to behave similarly to the leaf spring embodiments shown in FIGS. 12a and 12b is shown in FIG. 13. In the pneumatic embodiment of FIG. 13, valves are electronically closed to effectively increase the number of pneumatic springs in parallel.

The multiple parallel spring elements in FIGS. 12a, 12b, and FIG. 13 could equivalently be replaced by other types of spring elements, such as coil springs, torsion bars, elastomeric blocks, etc.

DETAILED DESCRIPTION

Figure 1:
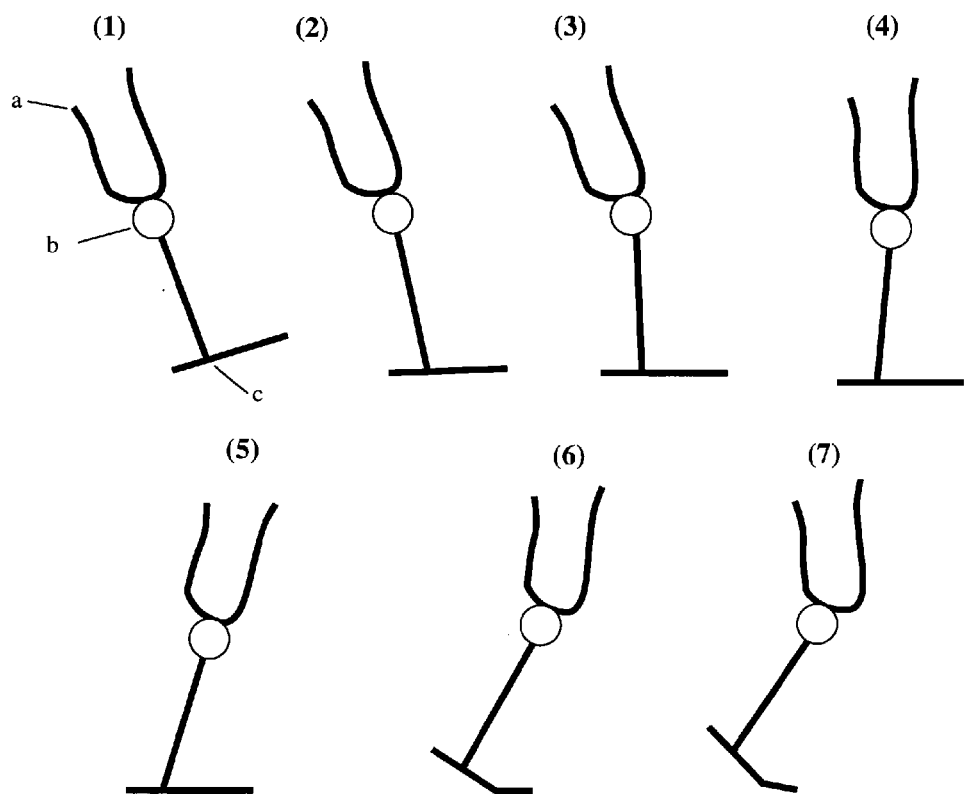
FIG. 1: Depiction of stages of a gait cycle, including controlled plantar-flexion, controlled dorsi-flexion, and powered plantar-flexion.
Figure 2:
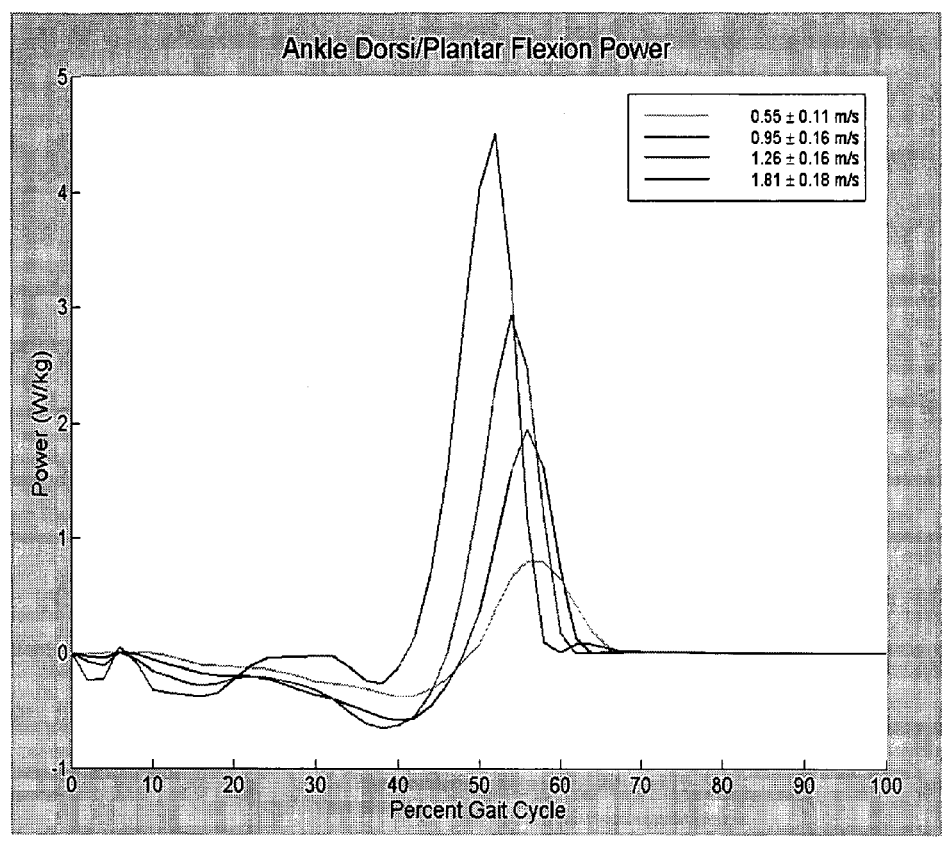
FIG. 2: Data from ten normal subjects are plotted showing mechanical power output versus percent gait cycle in walking. Both zero and one hundred percent gait cycle correspond to heel strike of the same foot
Figure 3:
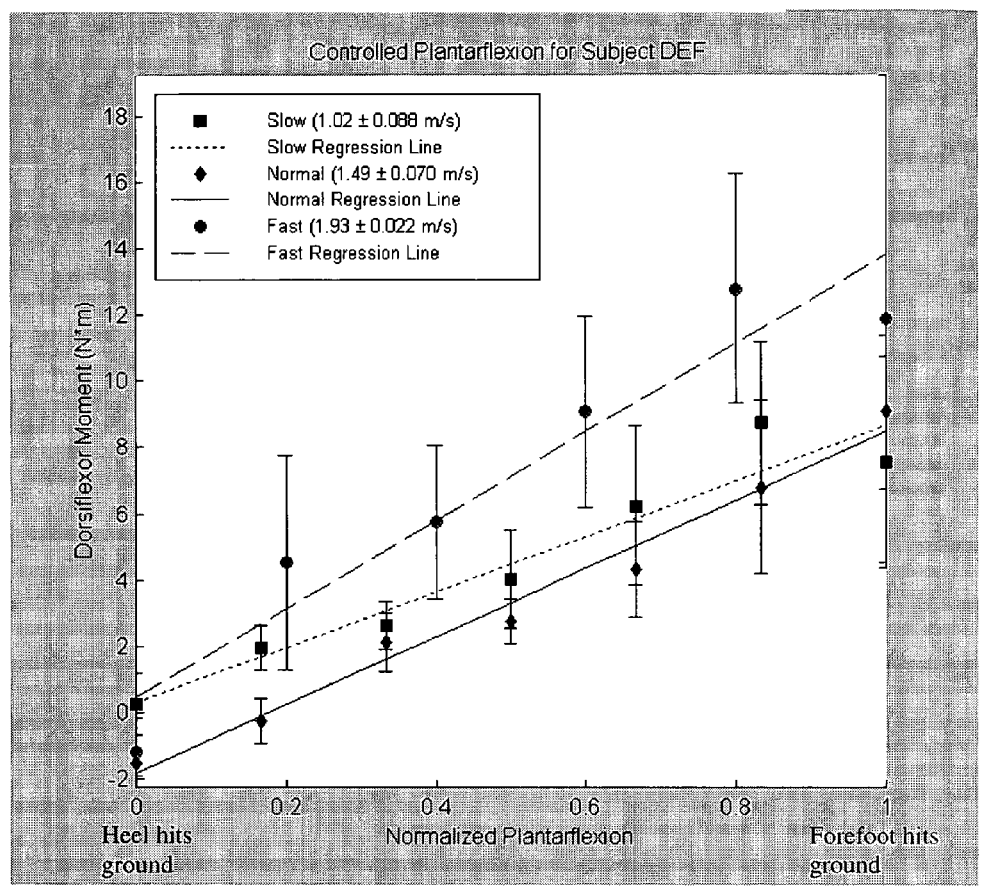
FIG. 3: Data for one subject, showing normal biological ankle function during the controlled plantar-flexion phase of walking.

A powered-catapult embodiment of the present invention is shown in FIGS. 4a-4d. FIG. 4a is a lumped-element model of a powered-catapult prosthetic. The mounted end 203 of the prosthesis attaches to the body, and the distal end 204 of the prosthesis interfaces to the environment (such as the ground for a leg prosthesis). Mounted end 203 is coupled to distal end 204 through spring 202, and through the series combination of force actuator 205 and force sensor 201. In some embodiments, displacement sensor 206 may also be included in parallel with spring 202. If the system is designed to operate in parallel with an existing limb, the muscles of the existing limb are modeled by muscle 200.

A mechanical implementation of lumped-element diagram 4a is shown in side view in FIG. 4c and in front view in FIG. 4d. In a preferred embodiment, during the portion of a gait cycle when the foot is not in contact with the ground, motor 205 turns spool 209 to wind on some of tension band 208, storing energy in spring 202. Force sensor 201 and winding distance sensor 207 may be used in a control loop to control how much energy is stored in spring 202, and how rapidly this energy is stored. Once the desired energy has been stored, clutch 207 is actuated to keep tension band 208 from unwinding and spring 202 from relaxing until the control system decides to release the stored energy. The energy stored in spring 202 during the swing phase of the gait cycle is represented by the dark area on the force vs. distance graph shown in FIG. 4b.

During the powered plantar-flexion phase of the gait cycle, the control system releases clutch 207, allowing the stored energy in spring 202 to be released, imitating the powered plantar-flexion stage of a normal gait cycle. This release of energy mimics the pulse of power put out by a biological ankle during the powered plantar-flexion stage of a walking or running gait cycle.

In an alternate embodiment, motor 205 may store energy in spring 202 at the same time as the natural leg stores impact energy during the gait cycle. This embodiment can be used to effectively implement one spring rate during compression (such as the spring rate depicted by the line from the origin to point Kd in FIG. 4b) and another spring rate during release (such as the spring rate depicted by the line from the origin to point Ks in FIG. 4b).

Figure 4:
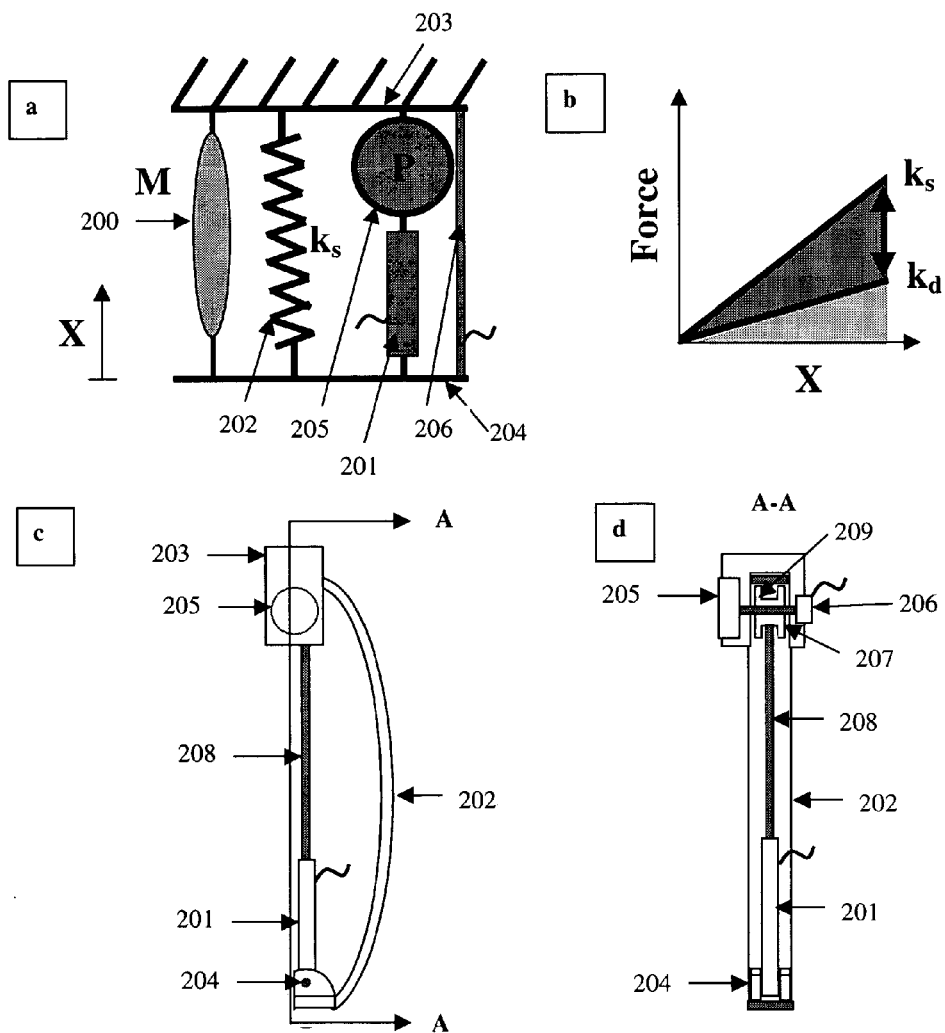
FIG. 4a: Basic catapult embodiment of the present invention, represented in terms of a lumped-parameter model.
FIG. 4b: Force-displacement graph where darkened area represents extra stored energy (used in walking/running) put into catapult system by force actuator while prosthetic foot is off the ground.
FIG. 4c: Side view of simplified prosthetic mechanism designed to provide powered plantar-flexion.
FIG. 4d: Front view of simplified prosthetic mechanism designed to provide powered plantar-flexion.
Figure 5:
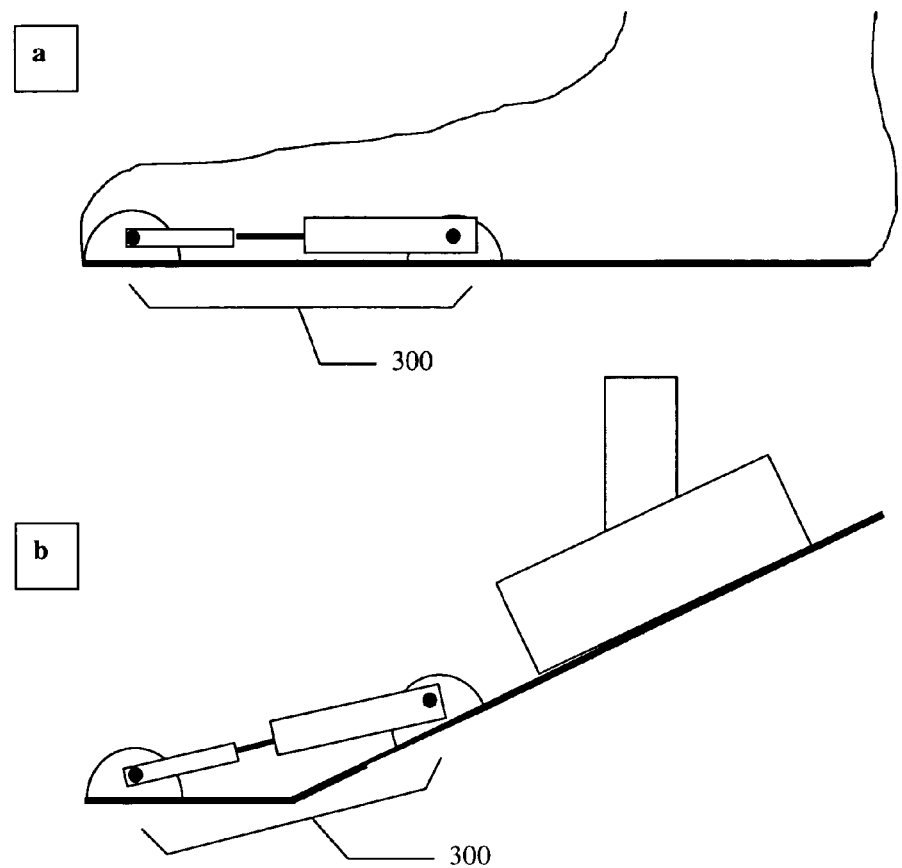
FIG. 5a: Catapult foot prosthesis or shoe orthosis for walking, running, and jumping, shown in the equilibrium configuration.
FIG. 5b: Catapult foot prosthesis or shoe orthosis for walking, running, and jumping, shown in a compressed state.

In an alternate embodiment, FIG. 5 shows a prosthetic foot or shoe orthosis that stores both muscle energy and motor energy in spring mechanism 300 during the gait cycle, for release during the powered plantar-flexion stage of the walking gait cycle (toe-off propulsion). When walking on this type of catapult prosthesis or foot orthosis, a person would experience a first (lower) spring rate (depicted by the line from the origin to point Kd in FIG. 4b), and a second (higher) spring rate (depicted by the line from the origin to point Ks in FIG. 4b) when releasing energy from spring 300 during the powered plantar-flexion phase of the gait cycle.

For catapult embodiments depicted in both FIG. 4 and in FIG. 5, part of the energy released during powered plantar-flexion came from leg muscle action compressing springs 202 and 300, and part came from an electromechanical actuator such as a motor. In a preferred embodiment of the present invention as depicted in FIG. 4, the majority of power stored in spring mechanisms by electromechanical actuators occurs during the minimal-load portion of the walking/running gait cycle (swing phase), and the start of the energy-release phase (late stance phase) of the gait cycle may be time-delayed with respect to the swing phase when motor energy is stored.

Figure 6:
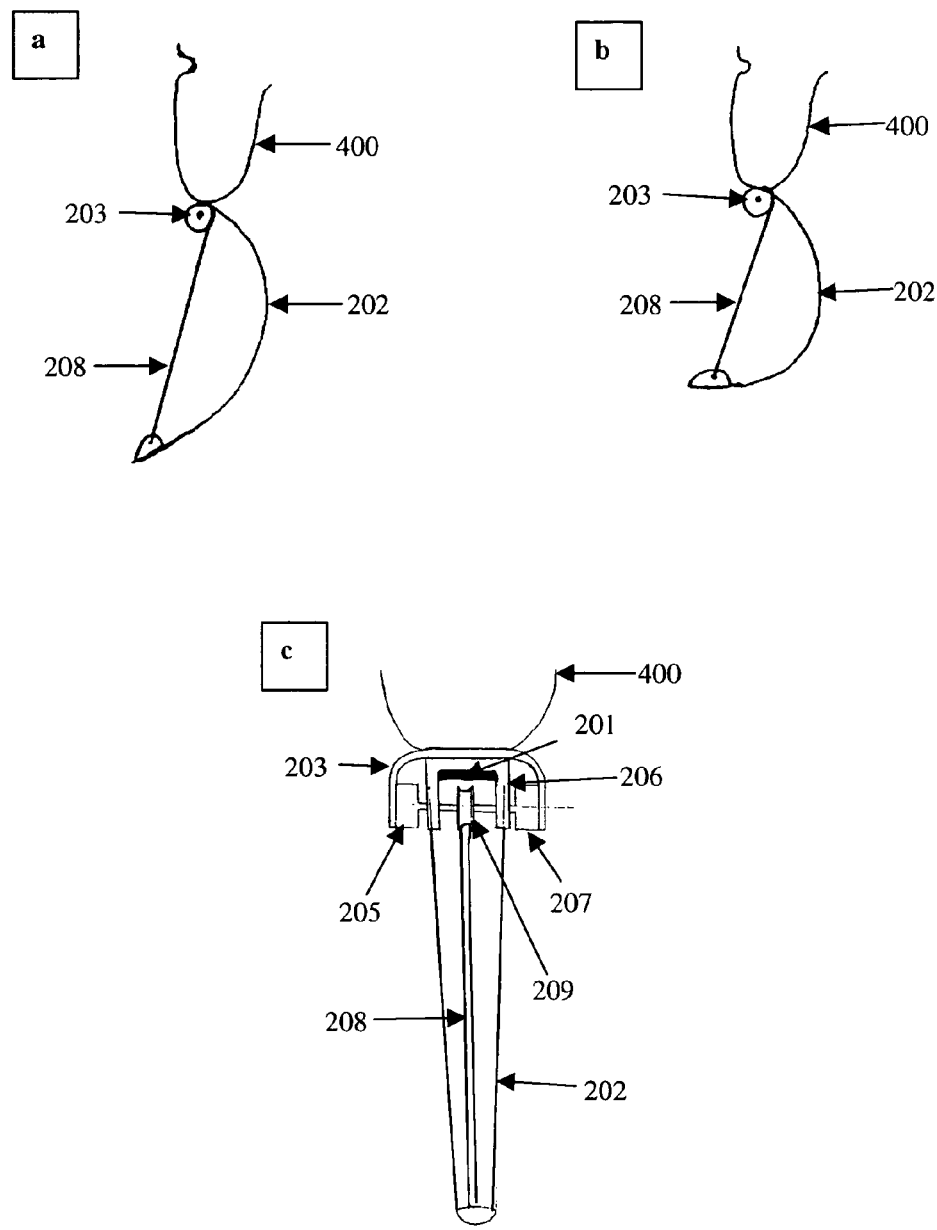
FIG. 6a: Side view of catapult leg prosthesis for walking, running, and jumping, shown in the equilibrium state.
FIG. 6b: Side view of catapult leg prosthesis for walking, running, and jumping, shown in a compressed state.
FIG. 6c: Front view of catapult leg prosthesis for walking, running, and jumping.

FIG. 6 is another depiction of the catapult leg prosthesis of FIG. 4, also showing socket 400, which attaches to the residual biological limb. Although the leg prostheses shown in FIGS. 4 and 6 are below-the-knee prostheses, the invention could also be employed in above-knee prostheses.

Figure 7:
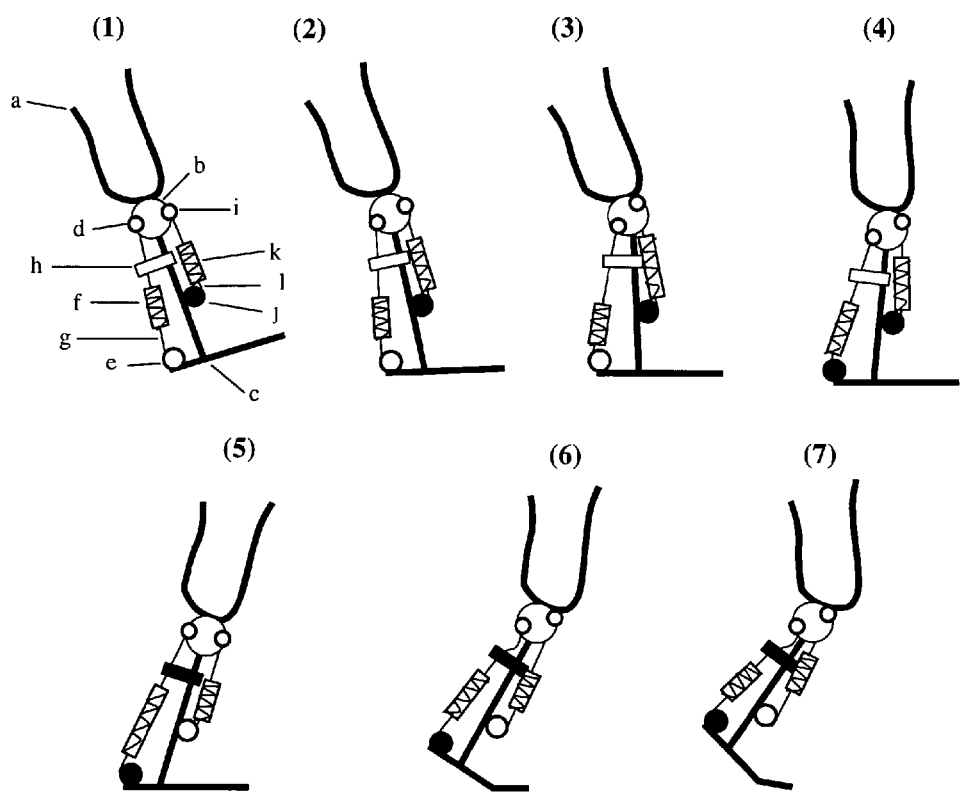
FIG. 7: An external, bi-articular transfemoral prosthesis or orthosis is shown in a heel strike to toe-off walking sequence. The system comprises springs and controllable clutches to transfer energy from hip muscular work to ankle powered plantar-flexion work.
Figure 8:
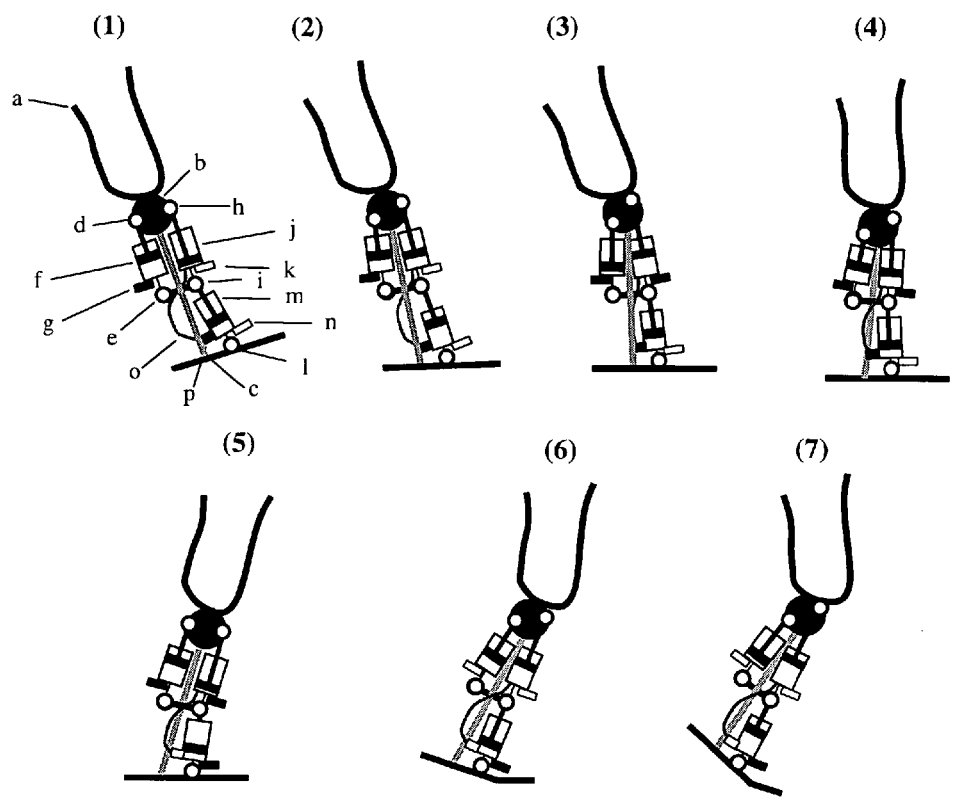
FIG. 8: An external, bi-articular transfemoral prosthesis or orthosis is shown in a heel strike to toe-off walking sequence. The system comprises pneumatic springs and controllable valves to transfer energy from hip muscular work to ankle powered plantar-flexion work.

Two bi-articular embodiments of the present invention are shown in FIGS. 7 and 8. In a first embodiment (FIG. 7), a prosthesis (above or below knee), robotic leg or full leg orthosis is shown having above-knee segment (a), knee joint (b), ankle joint (c), posterior knee pivot (d), posterior clutch (e), posterior spring (f), posterior cord (g), knee-ankle transfer clutch (h), anterior pivot (i), anterior clutch (j), anterior spring (k), and anterior cord (I). Anterior spring (k) stretches and stores energy during early stance knee flexion (from 1 to 3) and then releases that energy during early stance knee extension (from 3 to 5). Here spring (k) exerts zero force when the knee is fully extended, and anterior clutch (j) is engaged or locked throughout early stance knee flexion and extension (from 1 to 5). This stored energy, together with an applied extensor hip moment from either a robotic or biological hip, result in an extensor moment at the knee, forcing the knee to extend and stretching posterior spring (f) (from 3 to 5). The spring equilibrium length of posterior spring (f) is equal to the minimum distance from posterior knee pivot (d) to posterior clutch (e) (leg configuration 3 in FIG. 7). To achieve this spring equilibrium, posterior clutch (e) retracts posterior cord (g) as the distance from posterior knee pivot (d) to posterior clutch (e) becomes smaller. When this distance begins to increase in response to knee extension and ankle dorsi-flexion (from 4 to 5), posterior clutch (e) engages, causing posterior spring (f) to stretch. When the ankle is maximally dorsi-flexed and the knee fully extended (leg configuration 5), posterior spring (f) becomes maximally stretched. When the leg assumes this posture, knee-ankle transfer clutch changes from a disengaged state to an engaged state. Engaging the knee-ankle clutch mechanically grounds spring (f) below the knee rotational axis, and consequently, all the energy stored in spring (f) is transferred through the ankle to power ankle plantar-flexion (from 6 to 7). During late stance (from 5 to 6), the knee of the supporting leg begins to flex again in preparation for the swing phase. For this late stance knee flexion, anterior clutch (j) is disengaged to allow the knee to freely flex without stretching anterior spring (k).

It should be understood that the bi-articular knee-ankle invention of embodiment I (FIG. 7) could assume many variations as would be obvious to those of ordinary skill in the art. For example, the system described herein could act in parallel to additional ankle-foot springs and/or to an active or passive knee damper. Additionally, instead of mechanically grounding spring (f) distal to the knee axis to effectively transfer all the stored energy through the ankle, the perpendicular distance from the line of spring force (f) to the knee's axis of rotation could go to zero as the knee approaches full extension.

In a second embodiment (FIG. 8), a prosthesis (above or below knee), robotic leg or full leg orthosis is shown having a similar energy transfer from hip muscle extensors to artificial leg to power ankle plantar-flexion, accept energies are stored within pneumatic springs about the knee and then transferred to the ankle via a fluid transfer system. In this embodiment, the transfer of energy occurs without a physical bi-articular spring such as posterior spring (f) in FIG. 7. In this embodiment, anterior pneumatic spring (j) compresses and stores energy during early stance knee flexion (from 1 to 3). Here anterior knee valve (k) is closed or locked throughout early stance knee flexion and extension (from 1 to 5). This stored energy, together with an applied extensor hip moment from either a robotic or biological hip, result in an extensor moment at the knee, forcing the knee to extend and compress posterior pneumatic spring (f) (from 3 to 5). It is important to note that posterior knee valve (g) is open during early stance knee flexion so that posterior pneumatic spring (f) exerts little force. Knee valve (g) is then closed during knee extension so that energy is stored in the posterior pneumatic spring (f). When the ankle is maximally dorsi-flexed and the knee fully extended (leg configuration 5), posterior pneumatic spring (f) is maximally compressed. When the leg assumes this posture, knee-ankle transfer valve changes from a closed state to an open state, and anterior ankle valve (n) changes to a closed state, allowing all the energy stored in spring (f) is be transferred through the ankle to power ankle plantar-flexion (from 6 to 7). During late stance (from 5 to 6), the knee of the supporting leg begins to flex again in preparation for the swing phase. For this late stance knee flexion, anterior and posterior valves (g, k) are open to allow the knee to freely flex without compressing anterior spring (j).

It should be understood that the bi-articular knee-ankle invention of embodiment II (FIG. 8) could assume many variations as would be obvious to those of ordinary skill in the art. For example, the system described herein could act in parallel to active or passive ankle-foot springs and/or to an active or passive knee damper. Additionally, the energy in posterior pneumatic spring (f) could be transferred to a temporary holding chamber to be later released to the ankle during powered plantar-flexion.

Figure 9:
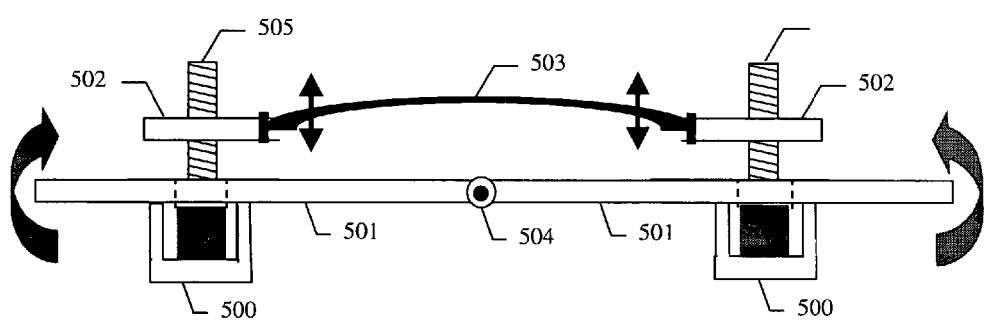
FIG. 9: Perpendicularly-variable-moment pivotal spring structure.

The mechanical system in FIG. 9 is a variable-mechanical-advantage embodiment of a variable-stiffness spring. Motors 500 and motor-driven screws 505 serve to change the moment of compression of bow spring 503 about pivot point 504. This mechanism may be used to adjust spring stiffness with minimal power under no-load conditions. It may also be used as an alternative way of storing energy in a spring which is under load, and thus may be used as a component of an immediate-release catapult system such as depicted in FIG. 5.

Figure 10:
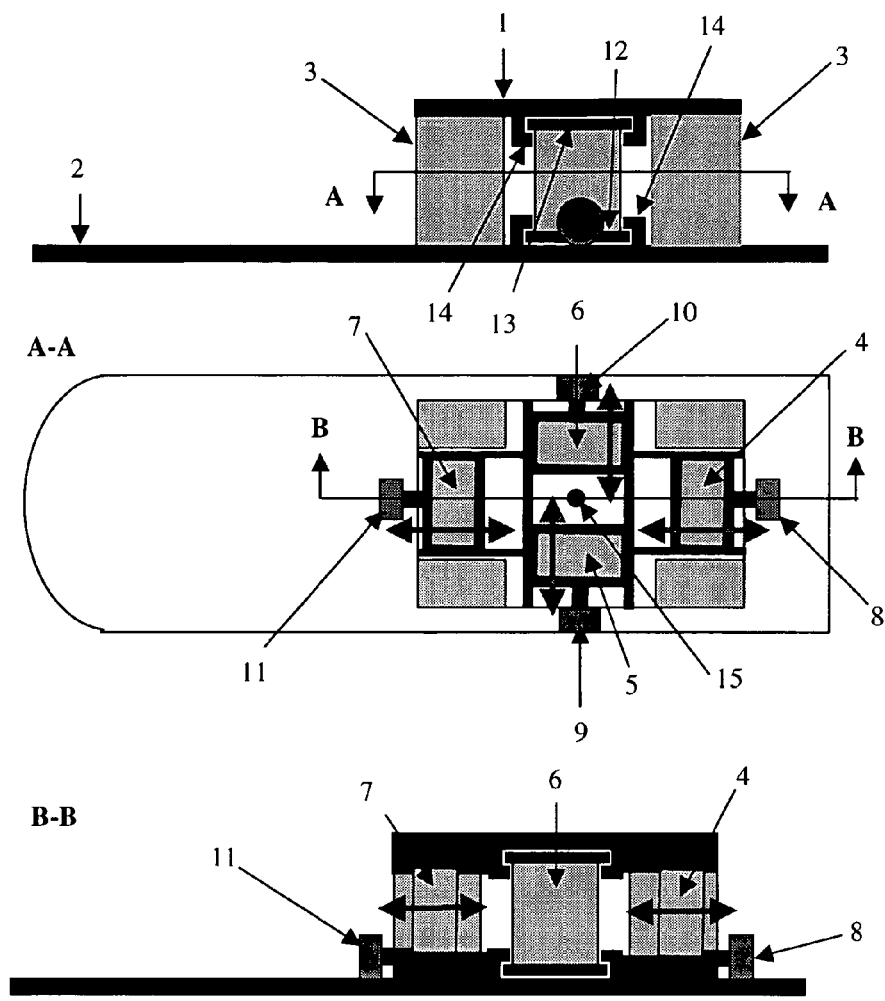
FIG. 10: Mechanical diagram of a low-profile prosthetic foot where spring elements are actively controlled (positioned) to affect ankle joint stiffness.

FIG. 10 depicts a low-profile prosthetic foot-ankle with top plate 1 and bottom plate 2, where spring elements are actively controlled (positioned) to affect ankle joint stiffness. This embodiment of the present invention is a variable-stiffness embodiment of the "variable mechanical advantage" subclass. In this low-profile prosthetic ankle joint embodiment, side-to-side spring rates of the prosthetic ankle and front-to-back spring rates of the prosthetic ankle are adjusted by varying the distance of spring elements 4, 5, 6, and 7 from the central pivot point 15 of the ankle joint. Spring top plates 13 and spring bottom plates 12 of spring elements 4, 5, 6, and 7 slide in tracks 14, driven by position-adjusting motors 8, 9, 10, and 11. In a preferred embodiment, motors 8, 9, 10, and 11 only change the positions of spring elements 4, 5, 6, and 7 when the ankle joint is under zero load (for instance, during the part of the walking gait when the foot is not in contact with the ground). Adjustment of spring position under zero load allows position adjustments to be done with minimal energy. This embodiment offers independent inversion/eversion stiffness control as well as independent plantar-flexion and dorsi-flexion control.

Figure 11:
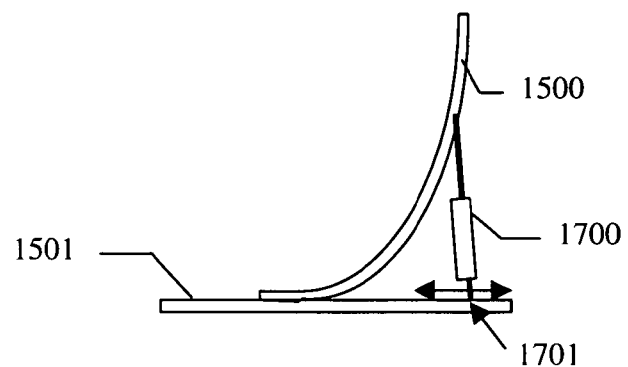
FIG. 11: Variable-stiffness joint according to the present invention, utilizing variable mechanical advantage to produce variable spring rate and/or variable damping rate.

A variable stiffness ankle-foot prosthesis embodiment according to the present invention is shown in FIG. 11. Constant-rate spring or damping element 1700 fixedly attached at one end and movably attached at the other end. Attachment point 1701 may be moved in and out with respect to the effective pivot point of the ankle joint. If element 1700 is a damping element, this configuration provides a variable damping ankle joint. If element 1700 is a spring element, this configuration provides a variable spring rate ankle joint. FIGS. 9, 10 and 11 demonstrate how a constant element can be transformed into a variable element according to the present invention, by varying mechanical advantage. In non-catapult preferred embodiments of the present invention, the variation in mechanical advantage takes place such that the motion used to vary the mechanical advantage takes place substantially perpendicular to the force the element being moved is under, thus minimizing the work needed to vary the mechanical advantage.

Figure 12:
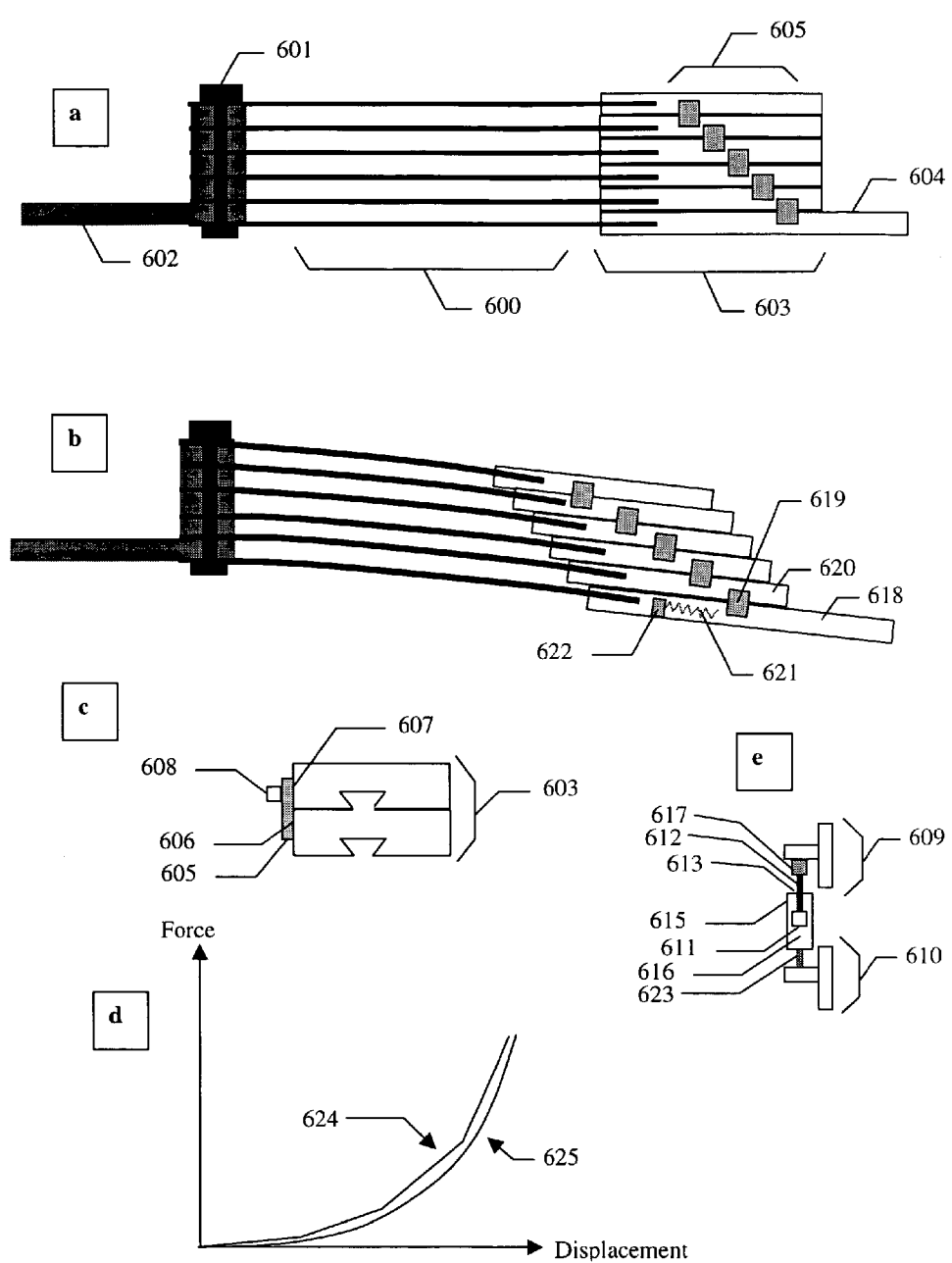
FIG. 12a: Multiply interlockable parallel leaf spring structure, shown in equilibrium position.
FIG. 12b: Multiply interlockable parallel leaf spring structure, shown in a stored-energy position.
FIG. 12c: End view of two dove-tailed slidably attached leaf spring terminations with controllable interlock actuator.
FIG. 12d: Piecewise-linear approximation to nonlinear spring function achieved by interlocking successive parallel leaf springs at various angles, and smoothed nonlinear spring function achieved by interlocking successive parallel leaf springs through coupling springs.
FIG. 12e: Nonlinear damping element coupling mechanism for coupling multiple spring elements.

FIGS. 12*a* and 12*b* depict a multiple-parallel-leaf-spring embodiment of a variable mechanical impedance according to the present invention. Leaf springs 600 are bound together and bound tightly to attaching bracket 602 at one end by bolt 601. At the other end, leaf springs terminate in slidably interlocking blocks 603, which may be locked together dynamically in pairs by interlocking plates 605. Each interlocking plate 605 is permanently bonded to one leaf spring terminator block 603 at surface interface 606, and controllably bindable to a second leaf spring terminator block 604 at a second interface 607, by binding actuator 608. Binding actuator 608 may bind surface interface 607 by any number of means such as mechanical clamp, pin-in-socket, magnetic clamp, etc. Adjacent leaf spring terminator blocks are slidably attached by dovetail slides or the like. The structure shown in FIGS. 12*a-c* can be used to implement a piecewise-linear spring function such as function 604 depicted in FIG. 12*d*, by engaging successive interlocks 605 at pre-determined points in spring flexure, and disengaging at like points.

In a preferred embodiment, the slope discontinuities in function 604 may be "smoothed" by coupling successive leaf springs through coupling springs. In FIG. 12*d*, stop plate 619 is affixed to leaf spring termination 620, and coupling spring 621 is mounted to leaf spring termination 618 through coupling spring mount 622. Leaf spring termination 620 is free to slide with respect to leaf spring termination 618 until coupling spring 621 and stop plate 619 come in contact. Coupling spring 621 acts to smooth the transition from the uncoupled stiffness of two leaf springs to the coupled stiffness of two leaf springs, resulting in smoothed force-displacement function 625 in FIG. 12*d*.

In a preferred embodiment, coupling spring 621 is itself a stiff, nonlinear spring. In another preferred embodiment, coupling spring 621 may have actively controllable stiffness, and may be made according to any of variable-stiffness spring embodiments of the present invention.

FIG. 12*e* depicts a non-linear dissipative coupling mechanism for coupling pairs of spring elements in a multiple-parallel-element spring. Mechanical mounts 609 and 610 affix to a pair of spring elements to be coupled. In a preferred embodiment, one of 609 and 610 is permanently affixed and the other of 609 and 610 is controllably affixed through a mechanism such as 608 described above. Piston 611 is coupled to mount 609 through rod 612 which passes through seal 614. Thus piston 611 may move back and forth in chamber 615 along the axis of rod 612. Chamber 615 is preferably filled with viscose or thixotropic substance 616. A viscose substance can be used in chamber 616 to provide a mechanical coupling force proportional to the square of the differential velocity between mounts 609 and 610. A thixotropic substance (such as a mixture of corn starch and water) can be used to provide an even more nonlinear relationship between coupling force and the differential velocity between coupling plates 609 and 610. Alternately, an electronically controlled variable damping element may be used in series with force sensor 617 between mounts 609 and 610, to provide an arbitrary non-linear dissipative coupling.

Utilizing a nonlinear dissipative coupling between pairs of elements in a multiple-parallel-element spring allows joint spring rates in a prosthetic limb which are a function of velocity. Thus, a joint spring rate can automatically become stiffer when running than it is while walking.

In one preferred embodiment, chamber 615 is rigidly mounted to mount 610. In another preferred embodiment, chamber 615 is mounted to mount 610 through coupling spring 623. In a preferred embodiment, coupling spring 623 may be an actively-controlled variable stiffness spring according to the present invention.

Figure 13:
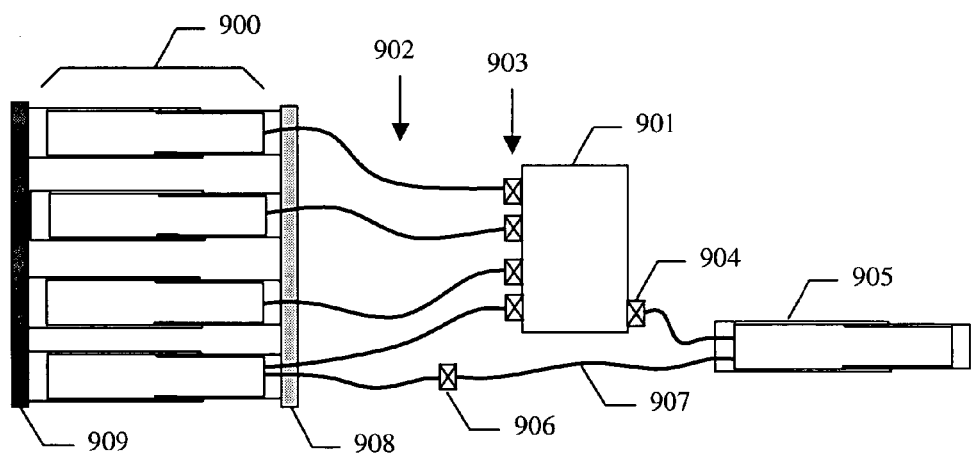
FIG. 13: Multiple-pneumatic-chamber variable spring rate and energy transfer system.

FIG. 13 depicts a multiple-couplable-parallel element pneumatic embodiment of the present invention. Multiple parallel pneumatic chambers 900 couple mounting plates 908 and 909. Pneumatic hoses 902 connect chambers 900 to a common chamber 901 through individually actuatable valves 903. Spring stiffness between plates 908 and 909 is maximized when all valves 903 are closed, and minimized when all valves 903 are open. Additional pneumatic element 905 may be added to transfer power from one prosthetic joint to another.

In an immediate-energy-transfer embodiment of the present invention according to FIG. 13, valves 904 and 906 may be timed to actuate in sequence with valves 903 to transfer power directly from chamber 905 to chambers 900. In a delayed-energy-transfer embodiment of the present invention according to FIG. 13, energy may be transferred from chamber 905 to chambers 900 or vice versa in a delayed manner, by chambers 900 or chamber 905 first pressurizing chamber 901, then isolating chamber 901 by closing valves 903 and 904 for some period of time, then transferring the energy stored in chamber 901 to chambers 900 or 905 by opening the appropriate valves.

Figure 15:
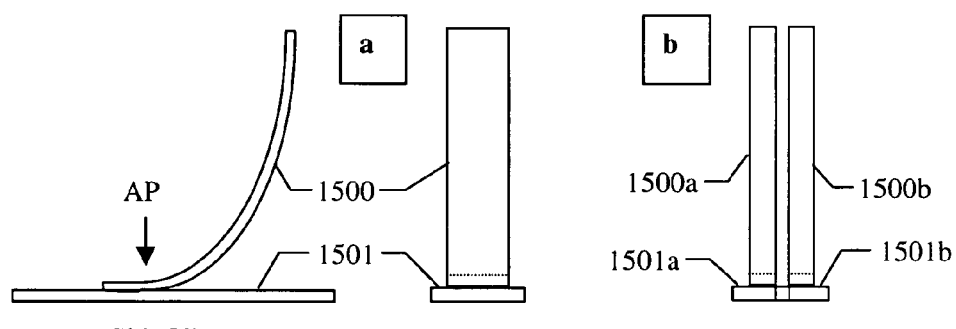
FIG. 15: Example prosthetic ankle/foot known in the art.

FIG. 15*a* depicts a prosthetic ankle-foot system known in the art. Ankle spring 1500 is affixed to foot-plate 1501. One variable-stiffness embodiment of the present invention shown in FIG. 15 uses a multiple-parallelly-interlockable-leaf-spring structure such as that shown in FIG. 12 in place of ankle spring 1500. Multiple-parallelly-interlockable-leaf-spring 1600 allows for different spring rates in forward and backward bending, allowing separately controllable rates of controlled plantar-flexion and controlled dorsi-flexion.

Figure 14:
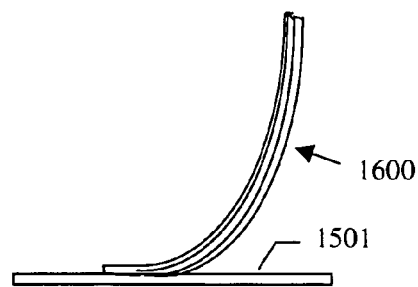
FIG. 14: Prosthetic ankle/foot utilizing multiple interlockable parallel leaf springs for ankle spring.

In one embodiment of the present invention (shown in FIG. 15*b*), ankle spring 1500 is split into inner ankle spring 1500*a*, and outer ankle spring 1500*b*, and heel spring 1501 is split rearward of attachment point AP into inner heel spring 1501*a* and outer heel spring 1501*b*. In a preferred embodiment, ankle springs 1500*a* and 1500*b* and heel springs 1501*a* and 1501*b* each comprise actively-variable multi-leaf springs such as ankle spring 1600 in FIG. 14. Having separate inner and outer variable-stiffness ankle springs allows for active control of side-to-side stiffness of the prosthetic ankle joint. Having separate inner and outer variable-stiffness heel springs allows for active control medio-lateral ankle stiffness.

Figure 16:
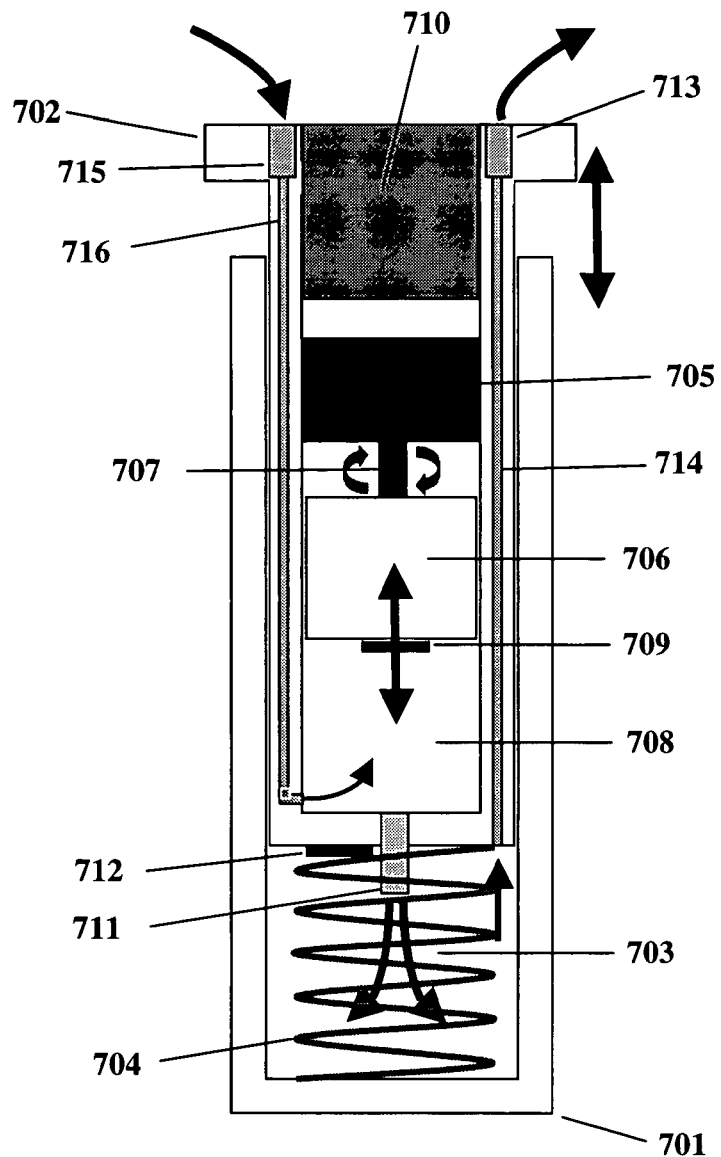
FIG. 16: Variable-stiffness pneumatic spring.

A pneumatic embodiment of a variable-stiffness spring for a prosthesis is shown in FIG. 16. Male segment 702 comprises one end of the overall variable-stiffness spring, and female segment 701 comprises the other end. Control electronics 710 are contained in the upper end of male segment 710. Intake valve 715 is actuatable to allow air to enter pressure chamber 708 through air intake channel 716 when pressure chamber 708 is below atmospheric pressure (or an external pump may be used to allow air to enter even when chamber 708 is above atmospheric pressure). Air pressure sensor 709 senses the pressure in pressure chamber 708. Pressure chamber 708 is coupled to second pressure chamber 703 through valve 711. The air in pressure chamber 703 acts as a pneumatic spring in parallel with spring 704. Motor 705 turns ball screw 707 to move piston 706 back and forth to control the volume of pressure chamber 708. Pressure in pressure chamber 703 may be lowered to a desired value by opening valve 703 for a controlled period of time, allowing air to escape through pressure release channel 714.

In one mode of operation, valve 711 is open and pressure chambers 708 and 703 combine to form a single pressure chamber. In this mode, movement of piston 706 directly controls the overall pressure chamber volume, and thus the overall pneumatic spring rate. In another mode of operation, valve 711 is closed, and valve 706 may be opened and piston 706 may withdrawn to add air to the system.

In a preferred embodiment of a variable-stiffness leg prosthesis according to the present invention is implemented through the pneumatic system of FIG. 16, motion of piston 706 occurs under minimal load, such as during the phase of gait when the foot is off the ground, or when the user is standing still.

The pneumatic system shown in FIG. 16 may also be used to implement immediate-release or delayed-release catapult embodiments of the present invention. An immediate-release catapult may be implemented by opening valve 711, and using motor 705 to add power (for instance, during the powered plantar-flexion phase of gait) as the power is needed. In a delayed-release catapult embodiment of the present invention, valves 715 and 711 are closed while motor 705 moves piston 706 to pressurize chamber 708, and then energy stored in chamber 708 is rapidly released during a phase of gait to produce the same effect as powered plantar-flexion.

In a preferred embodiment of the present invention, a pneumatic prosthetic leg element according to FIG. 16 is combined with the multiple controllably-couplable parallel leaf spring prosthetic ankle-foot of FIG. 15 to provide a prosthetic limb which provides powered plantar-flexion, controllable compressional leg spring stiffness, and controllable ankle stiffness during controlled plantar-flexion and controlled dorsi-flexion.

CLAIMS

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

Having described the invention, what is claimed is:

1. An autonomous motorized powered-catapult device having a mounted end adapted to be attached to a wearer's residual limb and an opposite distal end, said device comprising:
   a leg prosthesis having an ankle joint;
   an electromechanical actuator adapted to power the leg prosthesis, comprising:
      an elastic element configured to store elastic energy, and
      a motor operatively coupled to the elastic element;
   a sensor for sensing gait information; and
   a control system configured to cause the motor to store additional elastic energy in the elastic element as a function of information from the sensor for later release of stored energy from the elastic element to cause ankle powered plantar-flexion of the leg prosthesis thereby providing net positive mechanical work.

2. The device of claim 1, further comprising a clutch adapted to be actuated when the elastic energy is stored in the elastic element and adapted to allow release of the stored energy.

3. The device of claim 2, wherein the control system is configured to cause actuation and release of the clutch.

4. The device of claim 2, wherein the clutch is separate from the actuator.

5. The device of claim 1, wherein the control system is configured to cause the motor to store additional elastic energy in the elastic element and to release the stored energy from the elastic element during a gait cycle.

6. The device of claim 5, wherein the control system is configured to cause the motor to store additional elastic energy in the elastic element at the same time as a natural leg attached to the leg prosthesis stores energy during the gait cycle.

7. The device of claim 1, wherein the control system is configured to cause the motor to store additional elastic energy in the elastic element at the same time that the elastic element stores energy during a gait.

8. The device of claim 1, wherein the elastic element comprises a spring.

9. The device of claim 1, wherein an amount of energy stored in the elastic element by a natural leg attached to the leg prosthesis from compression is different than an amount of energy released from the elastic element to provide the ankle powered plantar-flexion of the leg prosthesis.

10. The device of claim 9, wherein the amount of energy stored in the elastic element by the natural leg attached to the leg prosthesis from compression is less than the amount of energy released from the elastic element to provide the ankle powered plantar-flexion of the leg prosthesis.

11. The device of claim 1, wherein the elastic element comprises a tension band.

12. The device of claim 1, wherein the sensed gait information comprises at least one of joint position, angular velocity and a phase of gait.

13. The device of claim 1, wherein the sensed gait information comprises at least one of angular displacement, linear displacement and force.

14. The device of claim 1, wherein the control system is configured to cause the motor to store additional elastic energy in the elastic element during a swing phase of gait.

15. The device of claim 1, wherein the control system is configured to cause the motor to store additional elastic energy in the elastic element during a minimal-load portion of gait.

16. The device of claim 1, wherein the elastic element comprises at least one end coupled to the motor.

17. The device of claim 1, wherein the elastic element is disposed in parallel with the motor.

18. The device of claim 1, wherein the elastic element couples the mounted end to the distal end.

19. The device of claim 1, wherein the control system is configured to cause the motor to operate in response to at least one of walking speed and ground irregularities.

20. The device of claim 1, wherein the actuator comprises a controllable mechanical impedance.

21. The device of claim 20, wherein the impedance of the actuator is controllable as a function of at least one of joint position, angular velocity and phase of gait.

22. The device of claim 1, wherein the actuator is configured to increase positive mechanical work or stiffness of the leg prosthesis as a function of at least one of locomotory speed and ground irregularities.

23. The device of claim 1, wherein the actuator is configured to increase peak mechanical power output of the leg prosthesis as a function of at least one of joint position, angular velocity and phase of gait.

24. The device of claim 1, wherein the sensor is a force sensor.

25. The device of claim 1, wherein the sensor is a displacement sensor.

* * * * *